United States Patent [19]
Klar et al.

[11] Patent Number: 6,025,507
[45] Date of Patent: Feb. 15, 2000

[54] BORNEOL DERIVATIVES, METHODS OF MANUFACTURING THEM, AND THEIR PHARMACEUTICAL USE

[75] Inventors: Ulrich Klar; Hernamm Graf; Günter Neef; Siegfried Blechert, all of Berlin, Germany

[73] Assignee: Schering Aktiengesellschaft, Berlin, Germany

[21] Appl. No.: 08/894,180

[22] PCT Filed: Feb. 19, 1996

[86] PCT No.: PCT/DE96/00297

§ 371 Date: Aug. 28, 1998

§ 102(e) Date: Aug. 28, 1998

[87] PCT Pub. No.: WO96/25392

PCT Pub. Date: Aug. 22, 1996

[30] Foreign Application Priority Data

Feb. 17, 1995 [DE] Germany ............... 195 06 885

[51] Int. Cl.[7] .......... C07D 303/16; C07C 271/22; A61K 31/325; A61K 31/335
[52] U.S. Cl. ............... 549/543; 560/23; 560/29; 514/475; 514/507
[58] Field of Search ............... 549/543; 560/23, 560/29; 514/507, 475

[56] References Cited

FOREIGN PATENT DOCUMENTS 253739 1/1998 European Pat. Off. .
4416374 11/1995 Germany .

Primary Examiner—Ba K. Trinh
Attorney, Agent, or Firm—Millen, White, Zelano & Branigan, P.C.

[57] ABSTRACT

Borneol derivatives of formula I

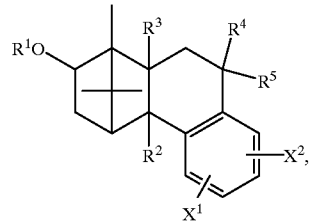

in which $R^1$ to $R^5$ and $X^1$ to $X^2$ are defined in the specification, and the method of making the same.

15 Claims, No Drawings

BORNEOL DERIVATIVES, METHODS OF MANUFACTURING THEM, AND THEIR PHARMACEUTICAL USE

This application is a 371 of PCT/DE 96/00297, dated Feb. 14, 1996.

The invention relates to new pharmacologically active compounds, which have the power to influence tubulin polymerization or tubulin depolymerization.

A number of natural mitotic poisons are used as antitumor agents or are undergoing clinical trials. Various classes of these mitotic poisons exist that exert their cytotoxic action either by inhibiting the polymerization of microtubuli in a spindle device (e.g., vinca alkaloids, colchicine) or accomplish this by a GTP-independent increase of the polymerization of the tubulin and prevention of the depolymerization of microtubuli (e.g., taxol, taxotere). Owing to previously little-understood physicochemical properties and the characteristics of neoplastic cells, mitotic poisons have a certain selectivity for tumor cells, but there is also significant cytotoxicity with regard to nontransformed cells.

Up until now, vinca alkaloids have had great importance in the combined chemotherapy of myeloid tumors. Taxanes have very recently opened up important applications that were not accessible by previously available cytostatic agents, e.g., ovarian cancers, malignant melanomas. The side effects of taxanes are comparable to those of other cytostatic agents, however (e.g., loss of hair, sensory neuropathy). Multi-drug-resistant tumor cells, which overexpress the P-glycoprotein, are resistant to taxanes. The limited availability of the natural substance taxol also inhibits its broader clinical trials.

Natural substances and synthetic pharmaceutical agents that have a spectrum of action unlike that of the previous mitotic poisons were therefore tested. An in vitro experimental arrangement makes it possible to search for substances that do not influence the GTP-dependent polymerization of tubulin, but influence the depolymerization of the microtubuli formed. Substances with such a profile of action should influence the versatile functions of microtubuli in extranuclear cell compartments less strongly than the dynamic of the spindle device during mitosis (metaphase/anaphase). Logically, such compounds should have fewer side effects in vivo than taxanes or vinca alkaloids.

Tubulin is an essential component of the mitotic spindle. It is used, i.a., to preserve the cell shape, to transport organelles inside the cell, and to influence cell mobility.

Up until now, taxanes have represented the only known structural class that is able to accelerate the polymerization of tubulin (mainly in the G2 phase), as well as to stabilize the microtubuli polymers formed. This mechanism is clearly distinguishable from those that have other structural classes which also influence the phase-specific cell division. Thus, for example, substances from the group of vinca alkaloids (e.g., vincristines and vinblastines) but also colchicine inhibit the polymerization of the tubulin dimers in the M phase.

It has now been found that compounds of formula I that are comparatively simple to produce are able to inhibit the depolymerization of microtubuli without increasing the formation of microtubuli in a GTP-independent manner. Moreover, compounds with a completely new profile of action that are able to accelerate the depolymerization of microtubuli were identified. On the basis of these properties, the compounds of formula I represent valuable pharmaceutical agents that are basically able to supplement or replace taxanes, which are difficult to synthesize and which are still not available in sufficient quantities, such as, e.g., taxol and Taxotere$^{(R)}$, in the treatment of malignant tumors (EP-A 253739).

The new borneol derivatives are characterized by general formula I

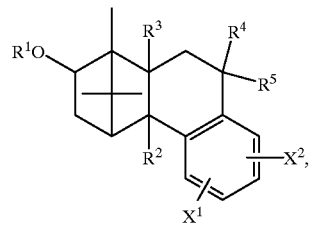

in which $R^1$ means $C(O)$—$CH(OR^6)$—$CH(NHR^{7a}R^{7b})$—$R^8$, $C(O)$—$CH(OR^{6a})$—$CH[NH(C(O)$—$CH(OR^{6b})$—$CH(NR^{7a}R^{7b})$—$R^8)]$—$R^8$, $R^2$ means hydrogen, —OH, $C_1$–$C_{10}$ alkyl, $C_1$–$C_{10}$ alkoxy, —OC(O)$R^{9a}$, —OSO$_2R^{9a}$, —OP(O)(OH)$_2$, NHR$^{9a}$, NR$^{9a}$R$^{9b}$, $R^3$ means hydrogen, —OH, $C_1$–$C_{10}$ alkoxy, —OC(O)$R^{9b}$, —OSO$_2R^{9b}$, —OP(O)(OH)$_2$, or $R^2$, $R^3$ together mean an oxygen atom, $R^4$ means hydrogen, $C_1$–$C_{10}$ alkyl, —$(CH_2)_n$—OR$^{11a}$, $R^5$ means hydrogen, $C_1$–$C_{10}$ alkyl, —$(CH_2)_p$—OR$^{11b}$, or $R^4$, $R^5$ together mean an oxygen atom, a =CHR$^{10}$ group, $R^{6a}$, $R^{6b}$ are the same or different and mean $R^6$, $R^{7a}$, $R^{7b}$ are the same or different and mean $R^7$, n means 0 to 8, p means 1 to 8, $R^7$ means —C(O)$R^{12}$, —SO$_2R^{12}$, —C(O)OR$^{12}$, —C(O)SR$^{12}$, —C(O)NHR$^{9d}$, —C(O)NR$^{9d}$R$^{9e}$, $C_1$–$C_{10}$ alkyl,

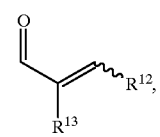

$R^8$ means phenyl, $R^{9a-e}$, $R^{12}$ are the same or different and mean $C_1$–$C_{10}$ alkyl, $C_4$–$C_8$ cycloalkyl, aryl, $C_7$–$C_{16}$ aralkyl, $R^{10}$ means hydrogen, $C_1$–$C_{10}$ alkyl, —$(CH_2)_s$—OR$^{14}$, s means 1 to 8, $R^6$, $R^{11a,b}$, $R^{14}$ are the same or different and mean hydrogen, $C_1$–$C_{10}$ alkyl, aryl, $C_1$–$C_{10}$ acyl, $C_7$–$C_{16}$ aralkyl, —SO$_2R^{9c}$, —P(O)(OH)$_2$, $R^{13}$, $R^{15a,b}$ are the same or different and mean hydrogen, $C_{1-C10}$ alkyl, aryl, $C_7$–$C_{16}$ aralkyl, $X^1$, $X^2$ are the same or different and mean X, X can be hydrogen, halogen, —OH, —NO$_2$, —N$_3$, —CN, —NR$^{15a}$R$^{15b}$, —NHSO$_2R^{15a}$, —CO$_2R^{15}$, $C_1$–$C_{10}$ alkyl, $C_1$–$C_{10}$ alkoxy, $C_1$–$C_{10}$ acyloxy, $C_1$–$C_{10}$ acyl, and, if $R^{15}$ means hydrogen, their salts with physiologically compatible bases, as well as their α-, β- or γ-cyclodextrin clathrates, as well as the compounds of general formula I that are encapsulated with liposomes.

The invention relates to the diastereomers and/or enantiomers of these borneol derivatives and also their mixtures.

As alkyl groups $R^2$, $R^4$, $R^5$, $R^6$, $R^{9a-e}$, $R^{10}$ $R^{11a,b}$, $R^{12}$, $R^{13}$, $R^{14}$, $R^{15a,b}$ and X, straight-chain or branched-chain alkyl groups with 1–10 carbon atoms can be considered, such as, for example, methyl, ethyl, propyl, isopropyl, butyl, isobutyl, tert-butyl, pentyl, isopentyl, neopentyl, heptyl, hexyl, decyl.

Alkyl groups $R^2$, $R^4$, $R^5$, $R^6$, $R^{9a-e}$, $R^{10}$, $R^{11a,b}$, $R^{12}$, $R^{13}$, $R^{14}$, $R^{15a,b}$, and X can be substituted by 1–3 halogen atoms, hydroxy groups, $C_1$–$C_4$ alkoxy groups, $C_6$–$C_{12}$ aryl groups, which can be substituted by 1–3 halogen atoms, di-($C_1$–$C_4$)-alkylamines and tri-($C_1$–$C_4$) alkylammonium.

As cycloalkyl groups $R^{9a-e}$, $R^{12}$, substituted and unsubstituted radicals with 4 to 8 carbon atoms are suitable.

As aryl radical $R^6$, $R^{9a-e}$, $R^{10}$, $R^{11a,b}$, $R^{12}$, $R^{13}$, $R^{14}$ $R^{15a,b}$, substituted and unsubstituted carbocyclic or heterocyclic radicals, such as, e.g., phenyl, naphthyl, furyl, thienyl, pyridyl, pyrazolyl, pyrimidinyl, oxazolyl, pyridazinyl, pyrazinyl, quinolyl, which can be substituted several times by the groups that are defined in X, are suitable.

The alkoxy, acyl and acyloxy groups that are contained in $R^2$, $R^3$ and X of general formula I are to contain 1 to 10 carbon atoms in each case, whereby methoxy, ethoxy, propoxy, isopropoxy, t-butyloxy, formyl, acetyl, propionyl and isopropionyl groups are preferred.

The $C_7$–$C_{16}$ aralkyl groups in $R^6$, $R^{9a-e}$, $R^{11a,b}$, $R^{12}$, $R^{13}$, $R^{14}$, $R^{15a,b}$, can contain up to 14 C atoms, preferably 6 to 10 C atoms, in the ring and 1 to 4 atoms, preferably 1 to 2 atoms, in the alkyl chain. Preferred aralkyl radicals are, e.g., benzyl, phenylethyl, naphthylmethyl or naphthylethyl. The rings can be substituted several times by the groups that are defined in X.

Free hydroxy groups in $R^1$, $R^2$, $R^3$, $R^4$, $R^5$, $R^{10}$ and X can be modified functionally, for example by etherification or esterification, whereby free hydroxy groups are preferred.

As ether and acyl radicals, the radicals that are known to one skilled in the art are suitable. Preferred are easily cleavable ether radicals, such as, for example, the tetrahydropyranyl, tetrahydrofuranyl, tert-butyldimethylsilyl, tert-butyldiphenylsilyl, tribenzylsilyl radical. As acyl radicals, e.g., acetyl, propionyl, butyryl, and benzoyl are suitable.

Halogen in the definitions of X means fluorine, chlorine, bromine and iodine.

For salt formation with the free acids ($R^{15}$=H), inorganic and organic bases are suitable, as they are known to one skilled in the art for the formation of physiologically compatible salts. For example, there can be mentioned: alkali hydroxides, such as sodium or potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

The invention also relates to a process for the production of borneol derivatives of formula I, which is characterized in that an olefin of general formula II

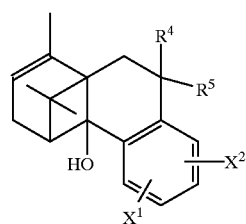

in which $R^4$, $R^5$, $X^1$ and $X^2$ have the above-mentioned meanings and are optionally protected in hydroxyl groups that are contained in $X^1$ or $X^2$, is epoxidated, and the epoxide formed is rearranged without isolation into an alcohol of general formula III

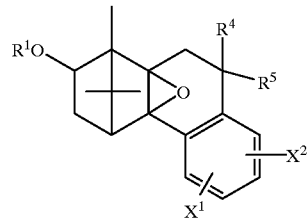

in which $R^4$, $R^5$, $X^1$ and $X^2$ have the above-mentioned meanings and hydroxyl groups that are contained in $R^1$, $X^1$ or $X^2$ are optionally protected, and this rearranged product is converted into a derivative of general formula I.

The reaction conditions of the above-named process stages are:

a) II→III

The epoxidation of the double bond is carried out with a peroxy compound, such as, e.g., meta-chloroperbenzoic acid, peroxotrifluoroacetic acid, hydrogen peroxide, tert-butyl hydroperoxide optionally with the addition of a Lewis acid, such as, e.g., titanium tetraisopropoxide in an inert solvent, such as, e.g., dichloromethane, toluene at −40° C. to +40° C. The reaction with tert-butyl hydroperoxide and titanium tetraisopropoxide in toluene at −10° C. to +25° C. is preferred.

The rearrangement of the epoxide formed is catalyzed by acids, such as, e.g., para-toluenesulfonic acid, silica gel, acid ion exchanger resins and hydrochloric acid. The use of silica gel is preferred.

b) III→I

The conversion of compounds of formula III into a compound of formula I can be carried out in various sequences:

1) Esterification of the alcohol function ($R^1$=hydrogen) →modification of $R^4$ and/or $R^5$→optionally epoxide opening, if $R^2$ and $R^3$ together represent an oxygen atom, optionally with subsequent modification of $R^2$ and $R^3$.

2) Esterification of alcohol function ($R^1$=hydrogen) →optionally epoxide opening, if $R^2$ and $R^3$ together represent an oxygen atom, optionally with subsequent modification of $R^2$ and $R^3$→modification of $R^4$ and/or $R^5$.

3) Protection of alcohol function ($R^1$=hydrogen) →optionally epoxide opening, if $R^2$ and $R^3$ together represent an oxygen atom, optionally with subsequent modification of $R^2$ and $R^3$→modification of $R^4$ and/or $R^5$→release and subsequent esterification of alcohol function ($R^1$=hydrogen).

4) Protection of alcohol function ($R^1$=hydrogen) →modification of $R^4$ and/or $R^5$→release and subsequent esterification of the alcohol function ($R^1$=hydrogen)→optionally epoxide opening, if $R^2$ and $R^3$ together represent an oxygen atom, optionally with subsequent modification of $R^2$ and $R^3$.

For esterification of the alcohol function ($R^1$=hydrogen), 1,4-diazabicyclo[2.2.2]octane (DABCO) is deprotonated with a base, such as, e.g., metal hydrides (e.g., sodium hydride), alkali alcoholates (e.g., sodium methanolate, potassium-tert-butanolate), alkali hexamethyl disilazane (e.g., sodium hexamethyl disilazane), 1,5-diazabicyclo[4.3.0]non-5-ene (DBN), 1,8-diazabicyclo[5.4.0]undec-7-ene (DBU), triethylamine, 4-(dimethylamino)pyridine (DMAP), and reacted with suitable carboxylic acid derivatives, such as, e.g., acid amides, acid halides, acid anhydrides in an inert solvent, such as, e.g., dichloromethane, diethyl ether, tetrahydrofuran at −70° C. to +50° C. Preferred is the reaction with sodium hexamethyl disilazane as a base, a cyclic acid amide as a carboxylic acid derivative, tetrahydrofuran as a solvent at temperatures of −40° C. to +25° C.

If $R^4$ and $R^5$ together represent a =$CHR^{10}$ group, the functionalization of the olefinic double bond can be carried out according to the methods that are known to one skilled in the art. For example, hydrogen can be stored, e.g., by catalyzed hydrogenation; hydroxyl groups can be introduced by water addition (hydroboration, oxymercurization) or by 1,2-bis-hydroxylation, e.g., with osmium tetroxide or potassium permanganate. The introduction of a carbonyl group ($R^4$, $R^5$ together represent an oxygen atom) is possible after cleavage of the double bond, e.g., by ozonolysis or by oxidative cleavage of a 1,2-diol. A carbonyl group that is produced in such a way can be used, for example, reduced, alkylated or as a carbonyl component in a Wittig reaction in building modified =$CHR^{10}$ groups.

If $R^2$ and $R^3$ together represent an oxygen atom, the epoxide can be reacted by nucleophiles, such as, for example, water, carboxylic acid derivatives (carboxylic acids, carboxylic acid halides, carboxylic anhydrides), sulfonic acid derivatives (sulfonic acids, sulfonic acid halides, sulfonic anhydrides), amines, in the presence of mineral or organic acids, such as, for example, hydrochloric acid, para-toluenesulfonic acid or Lewis acids, such as, for example, boron trifluoride etherate, titanium tetraisopropoxide, cerium ammonium nitrate either in inert solvents or as solvents that act as nucleophiles at −70° C. up to +50° C.

BIOLOGICAL EFFECTS AND APPLICATIONS OF NEW BORNEOL DERIVATIVES

The new compounds of formula I are valuable pharmaceutical agents. They interact with tubulin by stabilizing the microtubuli formed and are thus able to influence cell division in a phase-specific manner. This relates mainly to quick-growing, neoplastic cells, whose growth is largely unaffected by intercellular regulating mechanisms. Active ingredients of this type are mainly suitable for treating diseases in which the influence of cell division can be therapeutically indicated as is the case, e.g., in the treatment of Alzheimer's disease, malaria, treatment of diseases that are caused by gram-negative bacteria, as well as for treating malignant tumors. As applications for malignant tumors, for example, the treatment of ovarian, stomach, colon, adeno-, breast, lung, head and neck carcinomas, malignant melanoma, acute lymphocytic and myelocytic leukemia can be mentioned. The compounds according to the invention can be used by themselves or to achieve additive or synergistic actions in combination with other principles and classes of substances that can be used in tumor therapy.

As examples, there can be mentioned the combination with

Platinum complexes such as, e.g., cis-platinum, carboplatinum, intercalating substances, e.g., from the class of anthracyclins, such as, e.g., doxorubicin or from the class of anthrapyrazoles, such as, e.g., CI-941, substances that interact with tubulin, e.g., from the class of vinca alkaloids, such as, e.g., vincristine, vinblastine or from the class of taxanes, such as, e.g., taxol, taxotere or from the class of macrolides, such as, e.g., rhizoxin or other compounds, such as, e.g., colchicine, combretastatin A-4, DNA topoisomerase inhibitors, such as, e.g., camptothecin, etoposide, topotecan, teniposide, folate- or pyrimidine-antimetabolites, such as, e.g., lometrexol, gemcitubin, compounds that alkylate DNA, such as, e.g., adozelesin, dystamycin A, inhibitors of growth factors (e.g., of PDGF, EGF, TGFβ, EGF), such as, e.g., somatostatin, suramin, bombesin antagonists, inhibitors of protein tyrosine kinase or protein kinases A or C, such as, e.g., erbstatin, genisteine, staurosporine, ilmofosine, 8-Cl-cAMP, antihormones from the class of antigestagens, such as, e.g., mifepristone, onapristone, or from the class of antiestrogens, such as, e.g., tamoxifen, or from the class of antiandrogens, such as, e.g., cyproterone acetate, compounds that inhibit metastases, e.g., from the class of eicosanoids, such as, e.g., PGl , $PGE_1$, 6-oxo-$PGE_1$ as well as their more stable derivatives (e.g., iloprost, cicaprost, beraprost), inhibitors of the transmembrane $Ca^{2+}$ influx, such as, e.g., verapamil, galopamil, flunarizine, diltiazem, nifedipine, nimodipine, neuroleptic agents, such as, e.g., chlorpromazine, trifluoperazine, thioridazine, perphenazine, local anesthetics, such as, e.g., carbanilat-Ca7, cinchocaine, carbanilat-Ca3, articaine, carbanilat, lidocaine, substances that inhibit angiogenesis, such as, e.g., anti-VEGF-antibodies, endostatin B, interferon α, AGM 1470, inhibitors of cell proliferation in psoriasis, Kaposi's sarcoma, neuroblastoma.

The invention also relates to pharmaceutical agents that are based on pharmaceutically compatible compounds, i.e., compounds that are not toxic in the doses used, of general formula I, optionally together with the adjuvants and vehicles that are commonly used.

The compounds according to the invention can be worked into pharmaceutical preparations for enteral, percutaneous, parenteral or local administration according to methods of galenicals that are known in the art. They can be administered in the form of tablets, coated tablets, gel capsules, granulates, suppositories, implants, injectable sterile aqueous or oily solutions, suspensions or emulsions, ointments, creams and gels.

In this case, the active ingredient or active ingredients can be mixed with the adjuvants that are commonly used in galenicals, such as, e.g., gum arabic, talc, starch, mannitol, methyl cellulose, lactose, surfactants such as Tweens or Myrj, magnesium stearate, aqueous or non-aqueous vehicles, paraffin derivatives, wetting agents, dispersing agents, emulsifiers, preservatives and flavoring substances for taste correction (e.g., ethereal oils).

The invention thus also relates to pharmaceutical compositions, which as active ingredient contain at least one compound according to the invention. A dosage unit contains about 0.1–100 mg of active ingredient(s). In humans, the dosage e compounds according to the invention is approximately 0.1–1000 mg per day.

The embodiments below are used to explain the process according to the invention in more detail.

EXAMPLE 1

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 150 mg (214 μmol) of polar compound A that is presented according to Example 1a is dissolved under an atmosphere of dry argon in 7 ml of anhydrous tetrahydrofuran, mixed with 0.29 ml of a 1.1 M solution of tetrabutylammonium fluoride in tetrahydrofuran and stirred for 1 hour at 23° C. It is concentrated by evaporation, and the residue is purified by chromatography on about 40 ml of fine silica gel with a gradient system that consists of n-hexane and ethyl acetate. 113 mg (207 μmol, 97%) of the title compound is isolated as a colorless foam.

$^1$H-NMR (DMSO-d6, 80° C.): δ=0.78 (3H), 0.91 (3H), 1.02 (3H), 1.32 (9H), 1.58 (1H), 2.17 (1H), 2.75 (2H), 3.08 (1H), 4.36 (1H), 4.93 (1H), 5.01 (1H), 5.07 (1H), 5.33 (1H), 5.49 (1H), 6.53 (1H), 7.20–7.38 (7H), 7.56 (2H) ppm.

EXAMPLE 1a

[1R-[1α,2β(2R*,3S*),4α,4aβ,10aβ]]-3-[[(1,1-Dimethylethoxy)carbonyl]amino]-2-(triisopropylsilyloxy) benzenepropanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-[[(1,1-dimethylethoxy)carbonyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (B)

79 mg (280 μmol) of the mixture that is presented according to Example 1b as well as 176 mg of the β-lactam that is presented according to Example 1c are dissolved under an atmosphere of dry argon in 30 ml of anhydrous tetrahydrofuran, mixed at −35° C. with 0.34 ml of a 1 M solution of sodium hexamethyl disilazane in tetrahydrofuran and stirred for 15 more minutes. It is poured into saturated ammonium chloride solution, extracted several times with ethyl acetate, the combined organic extracts are washed with water and saturated sodium chloride solution and dried on sodium sulfate. The residue that is obtained after filtration and removal of solvent is separated by chromatography on about 70 ml of fine silica gel with a gradient system that consists of n-hexane and ethyl acetate. 26 mg (37 μmol, 13%) of title compound B is isolated as a nonpolar component, and 91 mg (130 μmol, 46%) of title compound A is isolated as a polar component, in each case as a colorless foam.

$^1$H-NMR (CDCl$_3$) of A: δ=0.8–1.47 (39H), 1.71 (1H), 2.22 (1H), 2.64 (1H), 2.71 (1H), 3.03 (1H), 4.66 (1H), 4.96 (1H), 5.02 (1H), 5.16 (1H), 5.47 (1H), 5.92 (1H), 7.16–7.54 (9H) ppm. $^1$H-NMR (CDCl$_3$) of B: δ=0.8–1.47 (39H), 1.79 (1H), 2.38 (1H), 2.68 (1H), 2.70 (1H), 3.15 (1H), 4.69 (1H), 5.06 (1H), 5.08 (1H), 5.22 (1H), 5.50 (1H), 5.71 (1H), 7.18–7.56 (9H) ppm.

EXAMPLE 1b

[1R-(1α,2β,4α,4aβ, 10aβ)]-9-Methylene-1,2,3,4,4a,9,10,10a-octahydro-1,12,12-trimethyl-4a,10a-epoxy-1,4-methanophenanthren-2-ol (A) and [1S-(1α,2β,4α,4aβ, 10aβ)]-9-methylene-1,2,3,4,4a,9,10,10a-octahydro-1,12,12-trimethyl-4a,10a-epoxy-1,4-methanophenanthren-2-ol (B)

2.1 g (7.88 mmol) of an approximately 7:3 mixture of [4R-(4α,4aβ,10aα)]-9-methylene-3,4,4a,9,10,10a-hexahydro-1,11,11-trimethyl-4,10a-methanophenanthren-4a-ol and [4S-(4a,4aβ,10aα)]-9-methylene-3,4,4a,9,10,10a-hexahydro-1,11,11-trimethyl-4,10a-methanophenanthren-4a-ol, which has been produced analogously to the process described on page 5879 in J. Am. Chem. Soc. 1992, is dissolved under an atmosphere of dry argon in 80 ml of anhydrous dichloromethane, and it is cooled to 0° C. It is mixed with 2.4 ml of titanium(IV) isopropylate, 1.5 ml of a 6.5 M anhydrous solution of tert-butyl hydroperoxide in toluene and stirred for 0.5 hour. It is poured into water, extracted several times with diethyl ether, the combined organic extracts are washed with water and saturated sodium chloride solution and dried on sodium sulfate. The residue that is obtained after filtration and removal of solvent is separated by chromatography on about 200 ml of fine silica gel with a gradient system that consists of n-hexane and ethyl acetate. 1.39 g (4.92 mmol, 62%) of title compounds A and B is isolated as a crystalline solid. By crystallization from diisopropyl ether, isomer A that is contained in excess in the product mixture can be obtained.

$^1$H-NMR (CDCl$_3$): δ=0.79 (3H), 0.88 (3H), 1.11 (3H), 1.58 (1H), 2.38 (1H), 2.68 (1H), 2.74 (1H), 3.08 (1H), 3.79 (1H), 3.97 (1H), 5.02 (1H), 5.48 (1H), 7.30 (2H), 7.51 (2H) ppm.

EXAMPLE 1c (3R ,4S)-1-[(1,1-Dimethylethoxy)carbonyl]-3-triisopropylsilyloxy-4-phenyl-2-azetidinone 2.5 g (7.82 mmol) of (3R,4S)-3-triisopropylsilyloxy-4-phenylazetidin-2-one, which has been produced analogously to the process that is described in Tetrahedron 48, 6985 (1992), is dissolved under an atmosphere of dry argon in 50 ml of anhydrous dichloromethane, cooled to 0° C., mixed with 3.1 ml of triethylamine, 3.65 ml of pyrocarbonic acid-di-tert-butyl ether as well as a catalytic amount of dimethylaminopyridine. It is allowed to heat to 23° C. and to stir for 16 hours. It is poured into saturated ammonium chloride solution, extracted several times with diethyl ether, the combined organic extracts are washed with water and saturated sodium chloride solution and dried on sodium sulfate. The residue that is obtained after filtration and removal of solvent is separated by chromatography on about 300 ml of fine silica gel with a gradient system that consists of n-hexane and ethyl acetate. 3.1 g (7.39 mmol, 94%) of the title compound is isolated as a crystalline solid.

$^1$H-NMR (CDCl$_3$): δ=0.80–1.02 (21H), 1.40 (9H), 5.07 (1H), 5.17 (1H), 7.27–7.40 (5H) ppm.

EXAMPLE 1d
(3R,4S)-1-Benzoyl-3-triisopropylsilyloxy-4-phenyl-2-azetidinone 5.0 g (15.6 mmol) of (3R,4S)-3-triisopropylsilyloxy-4-phenylazetidin-2-one, which has been produced analogously to the process that is described in Tetrahedron 48, 6985 (1992), is dissolved under an atmosphere of dry argon in 100 ml of anhydrous dichloromethane, cooled to 0° C., mixed with 6.2 ml of triethylamine, 3.85 ml of benzoyl chloride as well as a catalytic amount of dimethylaminopyridine. It is allowed to heat to 23° C. and to stir for 16 hours. It is poured into saturated ammonium chloride solution, extracted several times with diethyl ether, the combined organic extracts are washed with water and saturated sodium chloride solution and dried on sodium sulfate. The residue that is obtained after filtration and removal of solvent is separated by chromatography on about 400 ml of fine silica gel with a gradient system that consists of n-hexane and ethyl acetate. 6.43 g (15.2 mmol, 97%) of the title compound is isolated as a crystalline solid.

$^1$H-NMR (CDCl$_3$): δ=0.80–1.07 (21H), 5.25 (1H), 5.43 (1H), 7.27–7.43 (5H), 7.48 (2H), 7.59 (1H), 8.03 (2H) ppm.

EXAMPLE 1e
(3R,4S)-1-Cyclohexylcarbonyl-3-triisopropylsilyloxy-4-phenyl-2-azetidinone 2.0 g (6.3 mmol) of (3R,4S)-3-triisopropylsilyloxy-4-phenylazetidin-2-one, which has been produced analogously to the process that is described in Tetrahedron 48, 6985 (1992), is reacted analogously to Example 1d with use of cyclohexanecarboxylic acid chloride, and, after working-up and purification, 2.6 g (6.1 mmol, 96%) of the title compound is isolated.

$^1$H-NMR (CDCl$_3$): δ=0.81–1.03 (21H), 1.12–2.04 (10H), 3.03 (1H), 5.14 (1H), 5.19 (1H), 7.18–7.37 (5H) ppm.

EXAMPLE 1f
(3R,4S)-1-Acetyl-3-triisopropylsilyloxy-4-phenyl-2-azetidinone 2.0 g (6.3 mmol) of (3R,4S)3-triisopropylsilyloxy-4-phenylazetidin-2-one, which has been produced analogously to the process that is described in Tetrahedron 48, 6985 (1992), is reacted analogously to Example 1d with use of acetyl chloride, and, after working-up and purification, 1.8 g (5.0 mmol, 79%) of the title compound is isolated.

$^1$H-NMR (CDCl$_3$): δ=0.77–1.04 (21H), 2.45 (3H), 5.17 (1H), 5.22 (1H), 7.20–7.39 (5H) ppm.

EXAMPLE 1g
(3R,4S)-1-(1-Oxopropyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of propionic anhydride, and, after working-up and purification, 85 mg (226 μmol, 75%) of the title compound is isolated.

$^1$H-NMR (CDCl$_3$): δ=0.75–1.05 (21H), 1.18 (3H), 2.29 (2H), 5.14 (1H), 5.20 (1H), 7.20–7.39 (5H) ppm.

EXAMPLE 1h
(3R,4S)-1-(1-oxobutyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of butyric acid chloride, and, after working-up and purification, 103 mg (264 μmol, 88%) of the title compound is isolated.

$^1$H-NMR (CDCl$_3$): δ=0.75–1.07 (24H), 1.70 (2H), 2.76 (2H), 5.17 (1H), 5.20 (1H), 7.20–7.40 (5H) ppm.

EXAMPLE 1i
(3R,4S)-1-(1-Oxo-3-methylbutyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of 3-methylbutyric acid chloride, and, after working-up and purification, 106 mg (263 μmol, 88%) of the title compound is isolated.

$^1$H-NMR (CDCl$_3$): δ=0.74–1.05 (27H), 2.20 (1H), 2.58 (1H), 2.75 (1H), 5.16 (1H), 5.20 (1H), 7.20–7.38 (5H) ppm.

EXAMPLE 1k
(3R,4S)-1-(1-Oxo-3,3-dimethylbutyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of 3,3-dimethylbutyric acid chloride, and, after working-up and purification, 105 mg (251 μmol, 84%) of the title compound is isolated.

$^1$H-NMR (CDCl$_3$): δ=0.80–1.14 (30H), 2.62 (1H), 2.81 (1H), 5.15 (1H), 5.19 (1H), 7.22–7.38 (5H) ppm.

EXAMPLE 1l
(3R,4S)-1-(1-Oxo-3-phenylpropyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of 3-phenylpropionic acid chloride, and, after working-up and purification, 60 mg (133 μmol, 44%) of the title compound is isolated.

$^1$H-NMR (CDCl$_3$): δ=0.78–1.05 (21H), 2.92–3.25 (4H), 5.12 (1H), 5.17 (1H), 7.14–7.38 (10H) ppm.

EXAMPLE 1m
(3R,4S)-1-(1,4-Dioxo-4-methoxybutyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of succinic acid methyl ester chloride, and, after working-up and purification, 24 mg (55 μmol, 18%) of the title compound is isolated.

$^1$H-NMR (CDCl$_3$): δ=0.75–1.06 (21H), 2.66 (2H), 3.09 (2H), 3.67 (3H), 5.18 (1H), 5.23 (1H), 7.20–7.38 (5H) ppm.

EXAMPLE 1n
(3R,4S)-1-(1,4-Dioxo-4-hydroxybutyl)-3-triisopropylsilyloxy-4-phenyl-2-azetidinone 96 mg (300 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of succinic anhydride and, after working-up, 122 mg (300 μmol, 100%) of the title compound is isolated, which is further reacted without purification.

$^1$H-NMR (CDCl$_3$): δ=0.75–1.08 (21H), 2.72 (2H), 3.08 (2H), 5.18 (1H), 5.23 (1H), 7.20–7.40 (5H) ppm.

EXAMPLE 1o
(3R,4S)-1-(1-Oxo-3-Cyclopentylpropyl)-3-triisopropylsilyloxy-4-phenyl-2-azetidinone 200 mg (626 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of 3-cyclopentylpropionic acid chloride, and, after working-up and purification, 102 mg (230 μmol, 37%) of the title compound is isolated.

$^1$H-NMR (CDCl$_3$): δ=0.80–1.19 (23H), 1.42–1.86 (9H), 2.79 (2H), 5.15 (1H), 5.20 (1H), 7.20–7.38 (5H) ppm.

EXAMPLE 1p
(3R,4S)-1-(Methoxycarbonyl)-3-triisopropylsilyloxy-4-phenyl-2-azetidinone 200 mg (626 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of methyl chloroformate, and, after working-up and purification, 153 mg (405 μmol, 65%) of the title compound is isolated.

$^1$H-NMR (CDCl$_3$): δ=0.78–1.06 (21H), 3.80 (3H), 5.12 (1H), 5.20 (1H), 7.22–7.40 (5H) ppm.

EXAMPLE 1q
(3R,4S)-1-(Thiomethylcarbonyl)-3-[3-oxa-pent-2(RS)-yloxy]-4-phenyl-2-azetidinone 200 mg (626 μmol) of (3R,4S)-3-triisopropylsilyloxy-4-phenylazetidin-2-one, which has been produced analogously to the process that is described in Tetrahedron 48, 6985 (1992), is reacted analogously to Example 1d with use of chlorothioformic acid-S-methyl ester, and, after working-up and purification, 224 mg (569 μmol, 91%) of the title compound is isolated.

$^1$H-NMR (CDCl$_3$): δ=0.82–1.05 (21H), 2.37 (3H), 5.23 (2H), 7.22–7.40 (5H) ppm.

EXAMPLE 1r
(3R,4S)-1-(Ethoxycarbonyl)-3-triisopropylsilyloxy-4-phenyl-2-azetidinone 319 mg (1 mmol) of (3R,4S)-3-triisopropylsilyloxy-4-phenylazetidin-2-one, which has been produced analogously to the process that is described in Tetrahedron 48, 6985 (1992), is reacted analogously to Example 1d with use of ethyl chloroformate, and, after working-up and purification, 392 mg (1 mmol, 100%) of the title compound is isolated.

$^1$H-NMR (CDCl$_3$): δ=0.76–1.05 (21H), 1.27 (3H), 4.23 (2H), 5.11 (1H), 5.20 (1H), 7.22–7.40 (5H) ppm.

EXAMPLE 1s
(3R,4S)-1-(Thioethylcarbonyl)-3-[3-oxa-pent-2(RS)-yloxy]-4-phenyl-2-azetidinone 960 mg (3.0 mmol) of (3R,4S)-3-triisopropylsilyloxy-4-phenylazetidin-2-one, which has been produced analogously to the process that is described in Tetrahedron 48, 6985 (1992), is reacted analogously to Example 1d with use of chlorothioformic acid-S-ethyl ester, and, after working-up and purification, 1.11 g (2.72 mmol, 91%) of the title compound is isolated.

$^1$H-NMR (CDCl$_3$): δ=0.76–1.04 (21H), 1.28 (3H), 2.93 (2H), 5.21 (2H), 7.20–7.40 (5H) ppm.

EXAMPLE 1t
(3R,4S)-1-(Butoxycarbonyl)-3-triisopropylsilyloxy-4-phenylazetidin-2-one 96 mg (300 μmol) of (3R,4S)-3-triisopropylsilyloxy-4-phenyl-2-azetidinone, which has been produced analogously to the process that is described in Tetrahedron 48, 6985 (1992), is reacted analogously to Example 1d with use of butyl chloroformate, and, after working-up and purification, 106 mg (252 μmol, 84%) of the title compound is isolated.

$^1$H-NMR (CDCl$_3$): δ=0.76–1.04 (26H), 1.27 (1H), 1.57 (1H), 3.92 (1H), 4.15 (1H), 5.10 (1H), 5.20 (1H), 7.22–7.40 (5H) ppm.

EXAMPLE 2
[1S-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 26 mg (37 μmol) of nonpolar compound B that is presented according to Example 1a is reacted analogously to Example 1. After working-up and purification, 14 mg (25 μmol, 69%) of the title compound is obtained as a colorless oil.

$^1$H-NMR (CDCl$_3$): δ=0.84 (3H), 0.96 (3H), 1.08 (3H), 1.42 (9H), 1.83 (1H), 2.40 (1H), 2.70 (1H), 2.72 (1H), 3.18 (1H), 3.21 (1H), 4.58 (1H), 5.02 (1H), 5.10 (1H), 5.28 (1H), 5.50 (1H), 5.55 (1H), 7.22–7.38 (9H) ppm.

EXAMPLE 3
[1R-[1α,2β(2R*,3S*),4α,4aβ,10aβ]]-3-[Benzoylamino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 100 mg (142 μmol) of polar compound A that is presented according to Example 3a is reacted analogously to Example 1, and, after working-up and purification, 66 mg (120 μmol,85%) of the title compound is isolated as a colorless oil.

$^1$H-NMR (CDCl$_3$): δ=0.82 (3H), 0.91 (3H), 0.98 (3H), 1.81 (1H), 2.29 (1H), 2.68 (1H), 2.71 (1H), 2.91 (1H), 3.59 (1H), 4.71 (1H), 4.88 (1H), 5.13 (1H), 5.40 (1H), 5.71 (1H), 7.18 (2H), 7.22–7.40 (6H), 7.40–7.59 (4H), 7.70 (1H), 7.87 (2H) ppm.

EXAMPLE 3a
[1R-[1α,2β(2R*,3S*),4α,4aβ,10aβ]]-3-[Benzoylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-[benzoylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (B)

80 mg (283 μmol) of the mixture that is presented according to Example 1b as well as 181 mg of the β-lactam that is presented according to Example 1d are reacted analogously to Example 1a, and, after working-up and purification, 24 mg (34 μmol, 12%) of title compound B as a nonpolar component as well as 100 mg (142 μmol, 50%) of title compound A as polar component are isolated respectively as a colorless oil.

$^1$H-NMR (CDCl$_3$) of A: δ=0.8–1.22 (30H), 1.72 (1H), 2.20 (1H), 2.64 (1H), 2.66 (1H), 2.95 (1H), 4.78 (1H), 4.92 (1H), 5.05 (1H), 5.42 (1H), 5.68 (1H), 7.17–7.58 (12H), 7.65 (1H), 7.92 (2H) ppm.

$^1$H-NMR (CDCl$_3$) of B: δ=0.77 (3H), 0.80 (3H), 0.85–1.18 (24H), 1.65 (1H), 2.28 (1H), 2.53 (1H), 2.61 (1H), 2.79 (1H), 4.78 (1H), 5.02 (1H), 5.15 (1H), 5.46 (1H), 5.78 (1H), 7.11 (2H), 7.21–7.57 (10H), 7.74 (1H), 7.92 (2H) ppm.

EXAMPLE 4
[1S-[1α,2β(2R*,3S*),4α,4aβ,10aβ]]-3-[Benzoylamino]-2-hydroxybenzenepropanoic acid-9-methylene-1,2,3,4,4a,9, 10,10a-octahydro-1,12,12-trimethyl-4a,10a-epoxy-1,4-methanophenanthren-2-ylester 24 mg (34 μmol) of nonpolar compound B that is presented according to Example 3a is reacted analogously to Example 1, and, after working-up and purification, 10 mg (18 μmol, 54%) of the title compound is isolated as a colorless oil.

$^1$H-NMR (CDCl$_3$): δ=0.81 (3H), 0.90 (6H), 1.76 (1H), 2.32 (1H), 2.63 (1H), 2.67 (1H), 3.00 (1H), 3.34 (1H), 4.69 (1H), 5.07 (1H), 5.12 (1H), 5.47 (1H), 5.90 (1H), 7.16–7.58 (13H), 7.87 (2H) ppm.

EXAMPLE 5

[1S-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a-methoxy-10a-hydroxy-1,4-methanophenanthren-2-ylester 22 mg (30 μmol) of the compound that is presented according to Example 5a is reacted analogously to Example 1, and, after working-up and purification, 9 mg (16 μmol, 52%) of the title compound is isolated as a colorless foam.

$^1$H-NMR (CDCl$_3$): δ=0.65 (3H), 1.01 (6H), 1.43 (9H), 2.07 (1H), 2.41 (1H), 2.57 (1H), 2.73 (2H), 2.82 (3H), 3.27 (1H), 3.82 (1H), 4.51 (1H), 5.12 (1H), 5.21 (2H), 5.33 (1H), 6.23 (1H), 7.22–7.50 (9H) ppm.

EXAMPLE 5a

[1S-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a-methoxy-10a-hydroxy-1,4-methanophenanthren-2-ylester 20 mg (28 μmol) of nonpolar compound B that is presented according to Example 1a is dissolved in a mixture of 0.2 ml of dichloromethane and 2 ml of methanol, mixed with 200 mg of DOWEX 50 WX 4 and stirred under an atmosphere of dry argon for 5 hours at 23° C. It is filtered, the filtrate is washed with saturated sodium bicarbonate solution, saturated sodium chloride solution and dried on magnesium sulfate. After filtration and removal of solvent, 12 mg (16 μmol, 57%) of the title compound is isolated as a colorless oil, which is further reacted without purification.

$^1$H-NMR (CDCl$_3$): δ=0.64 (3H), 0.80–1.09 (27H), 1.44 (9H), 2.09 (1H), 2.43 (1H), 2.57 (1H), 2.68 (1H), 2.75 (1H), 2.80 (3H), 3.70 (1H), 4.60 (1H), 5.10 (1H), 5.12 (1H), 5.20 (1H), 5.34 (1H), 6.08 (1H), 7.17–7.49 (9H) ppm.

EXAMPLE 6

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a-methoxy-10a-hydroxy-1,4-methanophenanthren-2-ylester 15.6 mg (21 μmol) of the compound that is presented according to Example 6a is reacted analogously to Example 1, and, after working-up and purification, 8.6 mg (15 μmol, 71%) of the title compound is isolated as a colorless oil.

$^1$H-NMR (CDCl$_3$): δ=0.65 (3H), 1.01 (6H), 1.43 (9H), 2.17 (1H), 2.38 (1H), 2.58 (1H), 2.73 (2H), 2.86 (3H), 3.11 (1H), 3.92 (1H), 4.56 (1H), 5.11 (1H), 5.21 (2H), 5.35 (1H), 6.21 (1H), 7.20–7.50 (9H) ppm.

EXAMPLE 6a

[1R-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a-methoxy-10a-hydroxy-1,4-methanophenanthren-2-ylester 15 mg (21 μmol) of polar compound A that is presented according to Example 1a is reacted analogously to Example 5a, and, after working-up, 15.7 mg (21 μmol, 100%) of the title compound is isolated as a colorless oil, which is further reacted without purification.

$^1$H-NMR (CDCl$_3$): δ=0.63 (3H), 0.78–1.04 (27H), 1.43 (9H), 2.03 (1H), 2.30 (1H), 2.58 (1H), 2.68 (1H), 2.74 (1H), 2.80 (3H), 3.82 (1H), 4.69 (1H), 5.11 (1H), 5.14 (1H), 5.27 (1H), 5.34 (1H), 6.39 (1H), 7.16–7.48 (9H) ppm.

EXAMPLE 7

[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a-ethoxy-10a-hydroxy-1,4-methanophenanthren-2-ylester 16 mg (21 μmol) of the compound that is presented according to Example 7a is reacted analogously to Example 1, and, after working-up and purification, 7.8 mg (13 μmol, 63%) of the title compound is isolated as a colorless oil.

$^1$H-NMR (CDCl$_3$): δ=0.64 (3H), 1.01 (6H), 1.06 (3H), 1.41 (9H), 2.22–2.43 (2H), 2.58 (1H), 2.68–2.90 (3H), 2.93–3.13 (2H), 4.04 (1H), 4.56 (1H), 5.12 (1H), 5.18 (1H), 5.32 (2H), 6.36 (1H), 7.18–7.50 (9H) ppm.

EXAMPLE 7a

[1R-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a-ethoxy-10a-hydroxy-1,4-methanophenanthren-2-ylester 15 mg (21 μmol) of polar compound A that is presented according to Example 1a is reacted analogously to Example 5a with use of ethanol, and, after working-up, 16 mg (21 μmol, 100%) of the title compound, which is further reacted without purification, is isolated as a colorless oil.

$^1$H-NMR (CDCl$_3$): δ=0.63 (3H), 0.78–1.12 (30H), 1.43 (9H), 2.13–2.37 (2H), 2.57 (1H), 2.64–2.86 (3H), 3.08 (1H), 3.98 (1H), 4.69 (1H), 5.12 (2H), 5.33 (2H), 6.33 (1H), 7.15–7.48 (9H) ppm.

EXAMPLE 8

[1S-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a,10a-dihydroxy-1,4-methanophenanthren-2-ylester 6.5 mg (9.0 μmol) of the compound that is presented according to Example 8a is reacted analogously to Example 1 and after working-up and purification, 3.5 mg (6.2 μmol, 69%) of the title compound is isolated as a colorless oil.

$^1$H-NMR (CDCl$_3$): δ=0.69 (3H), 1.01 (3H), 1.07 (3H), 1.48 (9H), 2.26–2.49 (2H), 2.54 (1H), 2.76 (1H), 2.88 (1H), 3.25 (1H), 4.40 (1H), 4.54 (1H), 4.84 (1H), 5.08 (1H), 5.34 (1H), 5.37 (1H), 5.53 (1H), 5.65 (1H), 7.20–7.49 (9H) ppm.

EXAMPLE 8a

[1S-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a,10a-dihydroxy-1,4-methanophenanthren-2-ylester 14 mg (20 μmol) of nonpolar compound B that is presented according to Example 1a is dissolved in 1.5 ml of tetrahydrofuran, mixed with 0.5 ml of water, 3 drops of a 4N hydrochloric acid and stirred under an atmosphere of argon for 16 hours at 23° C. It is poured into saturated sodium bicarbonate solution, extracted with diethyl ether, washed with saturated sodium chloride solution and dried on magnesium sulfate. The residue that is obtained after filtration and removal of solvent is purified by chromatography on an analytical thin-layer plate. A mixture of n-hexane and ethyl acetate is used as a mobile solvent; diethyl ether is used as an eluant. 4.2 mg (5.8 μmol, 29%) of the title compound is isolated as a colorless foam, as well as 8.6 mg of starting material.

$^1$H-NMR (CDCl$_3$): δ=0.70 (3H), 0.80–1.08 (27H), 1.45 (9H), 2.31 (1H), 2.49 (1H), 2.54 (1H), 2.72 (1H), 2.86 (1H), 3.99 (1H), 4.54 (1H), 4.63 (1H), 5.08 (1H), 5.22–5.40 (3H), 5.75 (1H), 7.18–7.47 (9H) ppm.

EXAMPLE 9
[1R-[1α,2β(2R*,3S*),4α,4aβ,10aβ]]-3-[[(1,1-Dimethylethoxy)carbonyl]amino]-2-hydroxybenzenepropanoic acid-9-methylene-1,2,3,4,4a,9,10,10a-octahydro-1,11,11-trimethyl-4a,10a-dihydroxy-1,4-methanophenanthren-2-ylester 6.0 mg (8.3 μmol) of the compound that is presented according to Example 9a is reacted analogously to Example 1, and, after working-up and purification, 3.0 (5.3 μmol, 64%) of the title compound is isolated as a colorless oil.

$^1$H-NMR (CDCl$_3$): δ=0.71 (3H), 1.04 (6H), 1.40 (9H), 2.22–2.48 (2H), 2.57 (1H), 2.73 (1H), 2.89 (1H), 3.01 (1H), 3.12 (1H), 3.95 (1H), 4.54 (1H), 5.12 (1H), 5.21 (2H), 5.37 (1H), 5.93 (1H), 7.22–7.50 (9H) ppm.

EXAMPLE 9a
[1R-[1α,2β(2R*,3S*),4α,4aβ,10aβ]]-3-[[(1,1-Dimethylethoxy)carbonyl]amino]-2-(triisopropylsilyloxy)benzenepropanoic acid-9-methylene-1,2,3,4,4a,9,10,10a-octahydro-1,11,11-trimethyl-4a,10a-dihydroxy-1,4-methanophenanthren-2-ylester 15 mg (21.4 μmol) of polar compound A that is presented according to Example 1a is reacted analogously to Example 8a, and, after working-up and purification, 6 mg (8.3 μmol, 39%) of the title compound is isolated as a colorless oil.

$^1$H-NMR (CDCl$_3$): δ=0.70 (3H), 0.78–1.50 (36H), 2.18–2.40 (2H), 2.56 (1H), 2.71 (1H), 2.86 (1H), 3.26 (1H), 4.25 (1H), 4.68 (1H), 5.12 (2H), 5.34 (2H), 5.99 (1H), 7.16–7.47 (9H) ppm.

EXAMPLE 10
[1R-[1α,2β(2R*,3S*),4α,4aβ,10aβ]]-3-[[Cyclohexylcarbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 38 mg (53 μmol) of the compound that is presented according to Example 10a is reacted analogously to Example 1, and, after working-up and purification, 24 mg (43 μmol, 81%) of the title compound is isolated as a colorless oil.

$^1$H-NMR (CDCl$_3$): δ=0.60 (1H), 0.87 (3H), 0.93 (3H), 0.97–1.85 (14H), 2.22 (1H), 2.35 (1H), 2.76 (1H), 2.82 (1H), 3.10 (1H), 4.53 (1H), 5.08 (1H), 5.10 (1H), 5.47 (1H), 5.54 (1H), 7.19–7.45 (8H), 7.52 (1H), 7.58 (1H) ppm.

EXAMPLE 10a
[1R-[1α,2β(2R*,3S*),4α,4aβ,10aβ]]-3-[[Cyclohexylcarbonyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 15 mg (53 μmol) of compound A that is presented according to Example 1b and obtained enantiomer-free by crystallization as well as 34 mg of the β-lactam that is presented according to Example 1e are reacted analogously to Example 1a, and, after working-up, 44 mg of the title compound is isolated as crude product, which is further reacted without purification.

$^1$H-NMR (CDCl$_3$): δ=0.70–1.85 (40H), 2.22 (2H), 2.66 (1H), 2.78 (1H), 3.07 (1H), 4.64 (1H), 5.01 (1H), 5.09 (1H), 5.47 (1H), 5.53 (1H), 7.10–7.41 (9H), 7.49 (1H), 7.56 (1H) ppm.

EXAMPLE 11
[1R-[1α,2β(2R*,3S*),4α,4aβ,10aβ]]-3-[Acetylamino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 6.0 mg (9.3 μmol)

$^1$H-NMR (CDCl$_3$): δ=0.86 (3H), 0.93 (3H), 1.08 (3H), 1.74 (1H), 1.97 (3H), 2.35 (1H), 2.77 (1H), 2.83 (1H), 2.97 (1H), 3.09 (1H), 4.48 (1H), 4.97 (1H), 4.99 (1H), 5.52 (1H), 5.56 (1H), 7.19–7.42 (7H), 7.56 (2H), 7.61 (1H) ppm.

EXAMPLE 11a
[1R-[1α,2β(2R*,3S*),4α,4aβ,10aβ]]-3-[Acetylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthrene-2-ylester 5.6 mg (20 μmol) of compound A that is presented according to Example 1b and is obtained enantiomer-free by crystallization as well as 22 mg of the β-lactam that is presented according to Example 1f are reacted analogously to Example 1a, and, after working-up, 28 mg of the title compound is isolated as crude product, which is further reacted without purification.

$^1$H-NMR (CDCl$_3$): δ=0.81 (3H), 0.88 (3H), 0.95–1.30 (25H), 1.38 (1H), 1.98 (3H), 2.14 (1H), 2.65 (1H), 2.80 (1H), 3.08 (1H), 4.63 (1H), 4.93 (1H), 4.99 (1H), 5.50 (1H), 5.56 (1H), 7.15–7.38 (4H), 7.42–7.58 (4H), 7.67 (1H) ppm.

EXAMPLE 12
[1R-[1α,2β(2R*,3S*),4α,4aβ,10aβ]]-3-[(1-Oxopropyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 11 mg (17 μmol) of the compound that is presented according to Example 12a is reacted analogously to Example 1a. After working-up and purification, 3.0 mg (6.0 μmol, 35%) of the title compound is isolated as a colorless oil.

$^1$H-NMR (CDCl$_3$): δ=0.85 (3H), 0.93 (3H), 1.04 (3H), 1.08 (3H), 1.73 (1H), 2.22 (2H), 2.34 (1H), 2.77 (1H), 2.85 (1H), 2.99 (1H), 3.09 (1H), 4.48 (1H), 4.94 (1H), 5.01 (1H), 5.54 (1H), 5.58 (1H), 7.18–7.62 (10H) ppm.

EXAMPLE 12a
[1R-[1α,2β(2R*,3S*),4α,4aβ,10aβ]]-3-[(1-Oxopropyl)amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 10 mg (35 μmol) of compound A that is presented according to Example 1b as well as 20 mg of the β-lactam that is presented according to Example 1g are reacted analogously to Example 1a, and, after working-up and purification, 11 mg (17 μmol, 48%) of the title compound is isolated as a colorless oil.

$^1$H-NMR (CDCl$_3$): δ=0.81 (3H), 0.88 (3H), 0.95–1.28 (24H), 1.38 (1H), 2.15 (1H), 2.25 (2H), 2.64 (1H), 2.80 (1H), 3.07 (1H), 4.63 (1H), 4.93 (1H), 5.00 (1H), 5.52 (1H), 5.58 (1H), 7.15–7.60 (10H) ppm.

EXAMPLE 13
[1R-[1α,2β(2R*,3S*),4α,4aβ,10aβ]]-3-[(1-Oxobutyl)amino]-2-hydroxybenzenepropanoic acid-9-methylene-1,2, 3,4,4a,9,10,10a-octahydro-1,12,12-trimethyl-4a,10a-epoxy-1,4-methanophenanthren-2-ylester 7.0 mg (10 μmol) of the compound that is presented according to Example 13a is reacted analogously to Example 1a. After working-up and purification, 2.0 mg (3.9 μmol, 39%) of the title compound is isolated as a colorless oil.

$^1$H-NMR (CDCl$_3$): δ=0.73 (3H), 0.86 (3H), 0.93 (3H), 1.08 (3H), 1.54 (2H), 1.73 (1H), 2.18 (2H), 2.33 (1H), 2.75 (1H), 2.84 (1H), 3.03 (1H), 3.10 (1H), 4.49 (1H), 4.98 (1H), 5.03 (1H), 5.53 (1H), 5.57 (1H), 7.18–7.62 (10H) ppm.

EXAMPLE 13a

[1R-[1α,2β(2R*,3S*),4α,4aβ,10aβ]]-3-[(1-Oxobutyl)amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 10 mg (35 μmol) of compound A that is presented according to Example 1b as well as 21 mg of the β-lactam that is presented according to Example 1h are reacted analogously to Example 1a, and, after working-up and purification, 7 mg (10 μmol, 30%) of the title compound is isolated as a colorless oil.

$^1$H-NMR (CDCl$_3$): δ=0.72–1.28 (33H), 1.49 (1H), 1.54 (2H), 2.13 (1H), 2.20 (2H), 2.64 (1H), 2.80 (1H), 3.07 (1H), 4.63 (1H), 4.93 (1H), 5.02 (1H), 5.52 (1H), 5.58 (1H), 7.13–7.60 (10H) ppm.

EXAMPLE 14

[1R-[1α,2β(2R*,3S*),4α,4aβ,10aβ]]-3-[(3-Methyl-1-oxobutyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 12 mg (17 μmol) of the compound that is presented according to Example 14a is reacted analogously to Example 1a. After working-up and purification, 4.0 mg (7.6 μmol, 44%) of the title compound is isolated as a colorless oil.

$^1$H-NMR (CDCl$_3$): δ=0.63 (3H), 0.75 (3H), 0.86 (3H), 0.92 (3H), 1.08 (3H), 1.76 (1H), 1.92–2.18 (3H), 2.35 (1H), 2.76 (1H), 2.84 (1H), 2.98 (1H), 3.09 (1H), 4.52 (1H), 5.02 (1H), 5.07 (1H), 5.52 (1H), 5.55 (1H), 7.19–7.62 (10H) ppm.

EXAMPLE 14a

[1R-[1α,2β(2R*,3S*),4α,4aβ,10aβ]]-3-[(3-Methyl-1-oxobutyl)amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 10 mg (35 μmol) of compound A that is presented according to Example 1b as well as 21 mg of the β-lactam that is presented according to Example 1i are reacted analogously to Example 1a, and, after working-up and purification, 12 mg (18 μmol, 50%) of the title compound is isolated as a colorless oil.

$^1$H-NMR (CDCl$_3$): δ=0.64–1.30 (36H), 1.43 (1H), 1.96–2.22 (4H), 2.65 (1H), 2.80 (1H), 3.07 (1H), 4.63 (1H), 4.97 (1H), 5.05 (1H), 5.51 (1H), 5.58 (1H), 7.14–7.64 (10H) ppm.

EXAMPLE 15

[1R-[1α,2β(2R*,3S*),4α,4aβ,10aβ]]-3-[(3,3-Dimethyl-1-oxobutyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 12 mg (17 μmol) of the compound that is presented according to Example 15a is reacted analogously to Example 1a. After working-up and purification, 6.0 mg (11 μmol, 67%) of the title compound is obtained as a colorless oil.

$^1$H-NMR (CDCl$_3$): δ=0.73 (9H), 0.88 (3H), 0.94 (3H), 1.06 (3H), 1.81 (1H), 1.93 (1H), 2.21 (1H), 2.37 (1H), 2.76 (1H), 2.82 (1H), 2.93 (1H), 3.08 (1H), 4.52 (1H), 5.04 (1H), 5.08 (1H), 5.50 (1H), 5.53 (1H), 7.19–7.59 (10H) ppm.

EXAMPLE 15a

[1R-[1α,2β(2R*,3S*),4α,4aβ,10aβ]]-3-[(3,3-Dimethyl-1-oxobutyl)amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 10 mg (35 μmol) of compound A that is presented according to Example 1b as well as 22 mg of the β-lactam that is presented according to Example 1k are reacted analogously to Example 1a, and, after working-up and purification, 12 mg (17 μmol, 48%) of the title compound is isolated as a colorless oil.

$^1$H-NMR (CDCl$_3$): δ=0.80 (9H), 0.85 (3H), 0.89 (3H), 1.01 (3H), 1.04–1.31 (21H), 1.58 (1H), 1.97 (1H), 2.20 (1H), 2.25 (1H), 2.68 (1H), 2.79 (1H), 3.08 (1H), 4.63 (1H), 5.02 (1H), 5.07 (1H), 5.49 (1H), 5.57 (1H), 7.13–7.61 (10H) ppm.

EXAMPLE 16

[1R-[1α,2β(2R*,3S*),4α,4aβ,10aβ]]-3-[(3-Phenyl-1-oxopropyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 19 mg (26 μmol) of the compound that is presented according to Example 16a is reacted analogously to Example 1a. After working-up and purification, 9 mg (16 μmol, 60%) of the title compound is isolated as a colorless oil.

$^1$H-NMR (CDCl$_3$): δ=0.83 (3H), 0.90 (3H), 1.04 (3H), 1.59 (1H), 2.25 (1H), 2.44 (1H), 2.59 (1H), 2.70–89 (4H), 2.98 (1H), 3.03 (1H), 4.44 (1H), 4.81 (1H), 4.96 (1H), 5.20 (1H), 5.53 (1H), 6.84 (2H), 7.00 (2H), 7.03–7.23 (6H), 7.38 (2H), 7.45–7.52 (3H) ppm.

EXAMPLE 16a

[1R-[1α,2β(2R*,3S*),4α,4aβ,10aβ]]-3-[(3-Phenyl-1-oxopropyl)amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 10 mg (35 μmol) of compound A that is presented according to Example 1b as well as 60 mg of the β-lactam that is presented according to Example 1 1 are reacted analogously to Example 1a, and, after working-up and purification, 19 mg (26 μmol, 73%) of the title compound is isolated as a colorless oil.

$^1$H-NMR (CDCl$_3$): δ=0.75–1.32 (31H), 2.01 (1H), 2.48 (1H), 2.60 (1H), 2.64 (1H), 2.75 (1H), 2.84 (2H), 3.03 (1H), 4.56 (1H), 4.86 (1H), 4.93 (1H), 5.25 (1H), 5.54 (1H), 6.88 (2H), 7.00 (2H), 7.02 (2H), 7.05–7.30 (6H), 7.52 (2H), 7.64 (1H) ppm.

EXAMPLE 17

[1R-[1α,2β(2R*,3S*),4α,4aβ,10aβ]]-3-[(1,4-Dioxo-4-hydroxybutyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 25 mg (35 μmol) of the compound that is presented according to Example 17a is reacted analogously to Example 1a. After working-up and purification, 3.0 mg (5.5 μmol, 16%) of the title compound is isolated as a colorless oil.

$^1$H-NMR (CDCl$_3$): =0.68 (3H), 1.01 (3H), 1.03 (3H), 2.15 (1H), 2.40 (1H), 2.53 (1H), 2.55–2.69 (4H), 2.72 (1H), 2.82

(1H), 4.53 (1H), 5.08 (1H), 5.09 (1H), 5.33 (1H), 5.54 (1H), 7.20–7.47 (9H), 7.60 (1H) ppm.

EXAMPLE 17a
[1R-[1α,2β(2R*,3S*),4α,4aβ,10aβ]]-3-[(1,4-Dioxo-4-hydroxybutyl)amino]-2-(triisopropylsilyloxy) benzenepropanoic acid-9-methylene-1,2,3,4,4a,9,10,10a-octahydro-1,12,12-trimethyl-4a,10a-epoxy-1,4-methanophenanthren-2-ylester 10 mg (35 μmol) of compound A that is presented according to Example 1b as well as 36 mg of the β-lactam that is presented according to Example 1n are reacted analogously to Example 1a, and, after working-up, 49 mg of the title compound is isolated as crude product, which is further reacted without purification.

EXAMPLE 18
[1R-[1α,2β(2R*,3S*),4α,4aβ,9ξ,10aβ]]-3-[[(1,1-Dimethylethoxy)carbonyl]amino]-2-hydroxybenzenepropanoic acid-9-hydroxy-9-hydroxymethylene-1,2,3,4,4a,9,10,10a-octahydro-1,12,12-trimethyl-4a,10a-epoxy-1,4-methanophenanthren-2-ylester 5.5 mg (7.5 μmol) of the compound that is presented according to Example 18a is reacted analogously to Example 1a. After working-up and purification, 4.0 mg (6.9 μmol, 92%) of the title compound is isolated as a colorless oil.

$^1$H-NMR (CDCl$_3$): δ=0.83 (3H), 0.90 (3H), 1.11 (3H), 1.48 (9H), 1.65 (1H), 1.92 (1H), 2.32 (1H), 2.72 (1H), 3.02 (1H), 3.14 (1H), 3.19 (1H), 3.82 (1H), 3.95 (1H), 4.51 (1H), 4.73 (1H), 5.02 (1H), 5.47 (1H), 6.12 (1H), 7.20–7.58 (8H), 7.83 (1H) ppm.

EXAMPLE 18a
[1R-[1α,2β(2R*,3S*),4α,4aβ,9ξ,10aβ]]-3-[[(1,1-Dimethylethoxy)carbonyl]amino]-2-(triisopropylsilyloxy) benzenepropanoic acid-9-hydroxy-9-hydroxymethylene-1,2,3,4,4a,9,10,10a-octahydro-1,12,12-trimethyl-4a,10a-epoxy-1,4-methanophenanthren-2-ylester 10 mg (14 μmol) of compound A that is presented according to Example 1a is dissolved under an atmosphere of dry argon in 1.7 ml of acetone, mixed with 15 mg of N-methylmorpholino-N-oxide, 30 μl of a 2.5% solution of osmium tetroxide in t-butanol, 3.3 ml of water, and it is stirred at 40° C. for two days. It is mixed with 170 mg of sodium thiosulfate, extracted with diethyl ether, the organic phase is washed with water and dried on magnesium sulfate. The residue that is obtained after filtration and removal of solvent is purified by chromatography on an analytical thin-layer plate. A mixture of n-hexane and ethyl acetate is used as a mobile solvent; diethyl ether is used as an eluant. 5.5 mg (7.5 μmol, 55%) of the title compound is isolated as a colorless foam.

$^1$H-NMR (CDCl$_3$): δ=0.77 (3H), 0.82–1.34 (27H), 1.42 (1H), 1.47 (9H), 1.98 (1H), 2.13 (1H), 2.60 (1H), 3.10 (1H), 3.20 (1H), 3.74 (1H), 3.98 (1H), 4.63 (1H), 4.78 (1H), 5.07 (1H), 5.40 (1H), 6.21 (1H), 7.17–7.35 (4H), 7.41 (1H), 7.48 (1H), 7.54 (2H), 7.80 (1H) ppm.

EXAMPLE 19
[1R-[1α,2β(2R*,3S*),4α,4aβ,9β,10aβ]]-3-[[(1,1-Dimethylethoxy)carbonyl]amino]-2-hydroxybenzenepropanoic acid-9-methyl-1,2,3,4,4a,9,10,10a-octahydro-1,12,12-trimethyl-4a,10a-epoxy-1,4-methanophenanthren-2-ylester 11 mg (16 μmol) of the compound that is presented according to Example 19a is reacted analogously to Example 1a. After working-up and purification, 8.0 mg (14.6 μmol, 89%) of the title compound is isolated as a colorless oil.

$^1$H-NMR (CDCl$_3$): δ=0.78 (3H), 0.90 (3H), 1.02 (3H), 1.13–1.48 (12H), 1.78 (1H), 2.03 (1H), 2.19 (1H), 2.30 (1H), 2.66 (1H), 3.04 (1H), 3.25 (1H), 4.54 (1H), 4.95 (1H), 5.20 (1H), 5.93 (1H), 7.10–7.35 (6H), 7.47 (3H) ppm.

EXAMPLE 19a
[1R-[1α,2β(2R*,3S*),4α,4aβ,9β,10aβ]]-3-[[(1,1-Dimethylethoxy)carbonyl]amino]-2-(triisopropylsilyloxy) benzenepropanoic acid-9-methyl-1,2,3,4,4a,9,10,10a-octahydro-1,12,12-trimethyl-4a,10a-epoxy-1,4-methanophenanthren-2-ylester 10 mg (14 μmol) of compound A that is presented according to Example 1a is dissolved in 2 ml of ethanol, mixed with 2 mg of palladium on carbon (10%) and hydrogenated at 1 at under an atmosphere of hydrogen. After the theoretically calculated quantity is taken up, catalyst is filtered out, the filtrate is concentrated by evaporation, and the residue that is obtained is purified by chromatography on an analytical thin-layer plate. A mixture of n-hexane and ethyl acetate is used as a mobile solvent; diethyl ether is used as an eluant. 2.0 mg (2.8 μmol, 20%) of the title compound is isolated as a colorless foam.

$^1$H-NMR (CDCl$_3$): δ=0.75 (3H), 0.82–1.48 (39H), 1.68 (1H), 1.95–2.30 (3H), 2.60 (1H), 3.03 (1H), 4.63 (1H), 4.89 (1H), 5.21 (1H), 5.90 (1H), 7.08–7.50 (9H), ppm.

EXAMPLE 20
[1R-[1α,2β(2R*,3S*),4α,4aβ,10aβ]]-3-[3-Cyclopentyl-1-oxopropyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester (A) and
[1S-[1α,2β(2R*,3S*),4α,4aβ,10aβ]]-3-[3-Cyclopentyl-1-oxopropyl)amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester (B)

9.0 mg (12 μmol) of the diastereomer mixture that is presented according to Example 20a is reacted analogously to Example 1a. After working-up and purification, 2.3 mg (4 μmol, 34%) of title compound A is isolated as a more polar component as well as 1.1 mg (2 μmol, 16%) of title compound B as a more nonpolar component in each case as a colorless oil.

$^1$H-NMR (CDCl$_3$) of A: δ=0.87 (3H), 0.75–1.00 (2H), 0.93 (3H), 1.08 (3H), 1.2–1.7 (9H), 1.77 (1H), 2.08–2.41 (3H), 2.76 (1H), 2.84 (1H), 3.00 (1H), 3.10 (1H), 4.51 (1H), 5.02 (1H), 5.03 (1H), 5.51 (1H), 5.55 (1H), 7.18–7.61 (10H), ppm.

$^1$H-NMR (CDCl$_3$) of B: δ=0.73–1.02 (1H), 1.2–1.68 (9H), 1.80 (1H), 2.22 (2H), 2.37 (1H), 2.63 (1H), 2.70 (1H), 2.95 (1H), 3.18 (1H), 4.58 (1H), 5.03 (1H), 5.11 (1H), 5.47 (1H), 5.67 (1H), 6.95 (1H), 7.2–7.58 (9H), ppm.

EXAMPLE 20a
[1R-[1α,2β(2R*,3S*),4α,4aβ,10aβ]]-3-[3-Cyclopentyl-1-oxopropyl)amino]-2-(triisopropylsilyloxy) benzenepropanoic acid-9-methylene-1,2,3,4,4a,9,10,10a-octahydro-1,12,12-trimethyl-4a,10a-epoxy-1,4-methanophenanthren-2-ylester (A) and
[1S-[1α,2β(2R*,3S*),4α,4aβ,10aβ]]-3-[3-Cyclopentyl-1-oxopropyl)amino]-2-(triisopropylsilyloxy) benzenepropanoic acid-9-methylene-1,2,3,4,4a,9,10,10a-octahydro-1,12,12-trimethyl-4a,10a-epoxy-1,4-methanophenanthren-2-ylester (B)

20 mg (71 μmol) of the diastereomer mixture of compounds A and B that is presented according to Example 1b as well as 48 mg of the β-lactam that is presented according to Example 1o are reacted analogously to Example 1a, and, after working-up and purification, 27 mg (37 μmol, 52%) of a mixture of the two title compounds is isolated, which is further reacted without separation, as a colorless oil.

EXAMPLE 21
[1R-[1α,2β(2R*,3S*(2R*,3S*)],4α,4aβ,10aβ]]-3-[[3-(1-Oxobutyl)amino]-2-hydroxy-3-phenyl-1-oxopropyl]amino-2-hydroxybenzenepropanoic acid-9-methylene-1,2,3,4,4a,9,10,10a-octahydro-1,12,12-trimethyl-4a,10a-epoxy-1,4-methanophenanthren-2-ylester 9 mg (9.1 μmol) of the compound that is presented according to Example 21a is reacted analogously to Example 1a. After working-up and purification, 2 mg (2.9 μmol, 32%) of the title compound is isolated as a colorless oil.

$^1$H-NMR (CDCl$_3$): δ=0.82 (6H), 0.91 (3H), 1.01 (3H), 1.51 (2H), 1.76 (1H), 2.04 (2H), 2.28 (1H), 2.71–2.83 (2H), 3.03 (1H), 3.13 (1H), 3.53 (1H), 4.22 (1H), 4.42 (1H), 5.03 (1H), 5.10 (1H), 5.27 (1H), 5.42 (1H), 5.45 (1H), 6.62 (1H), 7.0–7.3 (10H), 7.38 (2H), 7.55 (2H), 7.93 (1H) ppm.

EXAMPLE 21a
[1R-[1α,2β(2R*,3S*(2R*,3S*)],4α,4aβ,10aβ]]-3-[[3-(1-oxobutyl)amino]-2-hydroxy-3-phenyl-1-oxopropyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 28 mg (100 μmol) of compound A that is presented according to Example 1b as well as 78 mg (2 equivalents) of the β-lactam that is presented according to Example 1h are reacted analogously to Example 1a, and, after working-up and purification, 9.0 mg (9.1 μmol, 9%) of the title compound is isolated as a colorless oil, as well as 53 mg of the compound that is described in Example 11a.

$^1$H-NMR (CDCl$_3$): δ=0.73 (3H), 0.75 (3H), 0.85–1.35 (48H), 1.52–1.73 (3H), 2.14 (1H), 2.21 (2H), 2.61 (2H), 2.86 (1H), 4.16 (1H), 4.55 (1H), 4.72 (1H), 4.91 (1H), 5.22 (1H), 5.38 (1H), 5.40 (1H), 7.09–7.35 (13H), 7.48 (2H), 7.91 (1H) ppm.

EXAMPLE 22
[1R-[1α,2β[2R*,3S*(2R*,3S*)],4α,4aβ,10aβ]]-3-[[3-(Acetylamino-2-hydroxy-3-phenyl-1-oxopropyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 25 mg (26 μmol) of the compound that is presented according to Example 22a is reacted analogously to Example 1a. After working-up and purification, 11 mg (17 μmol, 65%) of the title compound is isolated as a colorless oil.

$^1$H-NMR (CDCl$_3$): δ=0.83 (3H), 0.91 (3H), 1.01 (3H), 1.81 (1H), 1.86 (3H), 2.28 (1H), 2.45 (1H), 2.75 (1H), 2.78 (1H), 3.12 (1H), 3.6 (1H), 4.27 (1H), 4.40 (1H), 5.05 (1H), 5.10 (1H), 5.30 (1H), 5.42 (1H), 5.46 (1H), 6.67 (1H), 6.98–7.41 (12H), 7.53 (2H), 7.93 (1H) ppm.

EXAMPLE 22a
[1R-[1α,2β(2R*,3S*(2R*,3S*)],4α,4aβ,10aβ]]-3-[[3-Acetylamino-2-hydroxy-3-phenyl-1-oxopropyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 40 mg (142 μmol) of compound A that is presented according to Example 1b as well as 152 mg (3 equivalents) of the β-lactam that is presented according to Example 1f are reacted analogously to Example 1a, and, after working-up and purification, 25 mg (26 μmol, 18%) of the title compound is isolated as a colorless oil.

$^1$H-NMR (CDCl$_3$): δ=0.75 (3H), 0.77 (3H), 0.89 (3H), 0.94–1.23 (42H), 1.61 (1H), 2.02 (3H), 2.15 (1H), 2.56–2.68 (2H), 2.86 (1H), 4.20 (1H), 4.57 (1H), 4.73 (1H), 4.91 (1H), 5.24 (1H), 5.37 (1H), 5.40 (1H), 7.10–7.35 (13H), 7.48 (2H), 7.89 (1H) ppm.

EXAMPLE 23
[1R-[1α,2β(2R*,3S*),4α,4aβ,10aβ]]-3-(Methoxycarbonyl)amino-2-hydroxybenzenepropanoic acid-9-methylene-1,2,3,4,4a,9,10,10a-octahydro-1,12,12-trimethyl-4a,10a-epoxy-1,4-methanophenanthren-2-ylester 2.8 mg (4.2 μmol) of compound A that is presented according to Example 23a is reacted analogously to Example 1a. After working-up and purification, 2.0 mg (4.0 μmol, 94%) of the title compound is isolated as a colorless oil.

$^1$H-NMR (CDCl$_3$): δ=0.86 (3H), 0.92 (3H), 1.07 (3H), 1.75 (1H), 2.31 (1H), 2.73 (1H), 2.79 (1H), 3.06 (1H), 3.14 (1H), 3.65 (3H), 4.52 (1H), 4.89 (1H), 5.05 (1H), 5.26 (1H), 5.54 (1H), 6.62 (1H), 7.18–7.60 (9H) ppm.

EXAMPLE 23a
[1R-[1α,2β(2R*,3S*),4α,4aβ,10aβ]]-3-(Methoxycarbonyl)amino-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (A) and
[1S-[1α,2β(2R*,3S*),4α,4aβ,10aβ]]-3-(methoxycarbonyl)amino-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester (B)

10 mg (35 μmol) of a mixture of compounds A and B that are presented according to Example 1b as well as 20 mg of the β-lactam that is presented according to Example 1p are reacted analogously to Example 1a, and, after working-up and purification, 2.8 mg (4.2 μmol, 12%) of title compound A as well as 2.3 mg (3.5 μmol; 10%) of title compound B are isolated in each case as a colorless oil.

$^1$H-NMR (CDCl$_3$) of A: δ=0.70–1.20 (30H), 1.50 (1H), 2.18 (1H), 2.63 (1H), 2.26 (1H), 3.11 (1H), 3.65 (3H), 4.66 (1H), 4.88 (1H), 5.03 (1H), 5.24 (1H), 5.52 (1H), 6.64 (1H), 7.14–7.37 (5H), 7.42–7.59 (4H) ppm.

$^1$H-NMR (CDCl$_3$) of B: δ=0.72–1.10 (30H, 1.77 (1H), 2.37 (1H), 2.61–2.75 (2H), 3.05 (1H), 3.65 (3H), 4.71 (1H), 5.06 (1H), 5.08 (1H), 5.28 (1H), 5.52 (1H), 6.02 (1H), 7.20–7.59 (9H) ppm.

EXAMPLE 24
[1R-[1α,2β(2R*,3S*),4α,4aβ,10aβ]]-3-(Ethoxycarbonyl)amino-2-hydroxybenzenepropanoic acid-9-methylene-1,2,3,4,4a,9,10,10a-octahydro-1,12,12-trimethyl-4a,10a-epoxy-1,4-methanophenanthren-2-ylester 16 mg (23.7 μmol) of the compound that is presented according to Example 24a is reacted analogously to Example 1a. After working-up and purification, 7 mg (13.5 μmol, 57%) of the title compound is isolated as a colorless oil.

$^1$H-NMR (CDCl$_3$): δ=0.85 (3H), 0.92 (3H), 1.07 (3H), 1.21 (3H), 1.77 (1H), 2.30 (1H), 2.71 (1H), 2.78 (1H), 3.11 (1H), 3.15 (1H), 4.11 (2H), 4.53 (1H), 4.93 (1H), 5.06 (1H), 5.27 (1H), 5.52 (1H), 6.38 (1H), 7.18–7.37 (5H), 7.42–7.60 (4H) ppm.

EXAMPLE 24a
[1R-[1α,2β(2R*,3S*),4α,4aβ,10aβ]]-3-(Ethoxycarbonyl)amino-2-(triisopropylsilyloxy)benzenepropanoic acid-9- methylene-1,2,3,4,4a,9,10,10a-octahydro-1,12,12-trimethyl-4a,10a-epoxy-1,4-methanophenanthren-2-ylester 50 mg (177 μmol) of compound A that is presented according to Example 1b as well as 114 mg of the β-lactam that is presented according to Example 1r are reacted analogously to Example 1a, and, after working-up and purification, 119 mg (176 μmol, 100%) of the title compound is isolated as a colorless oil.

$^1$H-NMR (CDCl$_3$): δ=0.72–1.34 (33H), 1.53 (1H), 2.19 (1H), 2.63 (1H), 2.73 (1H), 3.10 (1H), 4.11 (2H), 4.67 (1H), 4.90 (1H), 5.03 (1H), 5.24 (1H), 5.52 (1H), 6.38 (1H), 7.12–7.35 (5H), 7.39–7.58 (4H) ppm.

EXAMPLE 25

[1R-[1α,2β(2R*,3S*),4α,4aβ,10aβ]]-3-(Butoxycarbonyl) amino-2-hydroxybenzenepropanoic acid-9-methylene-1,2,3,4,4a,9,10,10a-octahydro-1,12,12-trimethyl-4a,10a-epoxy-1,4-methanophenanthren-2-ylester 9 mg (13 μmol) of the compound that is presented according to Example 25a is reacted analogously to Example 1a. After working-up and purification, 5 mg (9 μmol, 70%) of the title compound is isolated as a colorless oil.

$^1$H-NMR (CDCl$_3$): δ=0.60–1.00 (9H), 1.07 (3H), 1.31 (2H), 1.58 (2H), 1.78 (1H), 2.30 (1H), 2.71 (1H), 2.77 (1H), 3.03–3.25 (2H), 3.81 (1H), 4.04 (1H), 4.54 (1H), 4.97 (1H), 5.06 (1H), 5.25 (1H), 5.51 (1H), 6.30 (1H), 7.16–7.60 (9H) ppm.

EXAMPLE 25a

[1R-[1α,2β(2R*,3S*),4α,4aβ,10aβ]]-3-(Butoxycarbonyl) amino-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 5 mg (18 μmol) of compound A that is presented according to Example 1b as well as 12 mg of the β-lactam that is presented according to Example 1t are reacted analogously to Example 1a, and, after working-up and purification, 9.5 mg (13.5 μmol, 75%) of the title compound is isolated as a colorless oil.

$^1$H-NMR (CDCl$_3$): δ=0.75–1.18 (33H), 1.29 (2H), 1.48–1.66 (3H), 2.19 (1H), 2.63 (1H), 2.72 (1H), 3.08 (1H), 3.82 (1H), 4.04 (1H), 4.67 (1H), 4.91 (1H), 5.02 (1H), 5.22 (1H), 5.48 (1H), 6.31 (1H), 7.14–7.57 (9H) ppm.

EXAMPLE 26

[1R-[1α,2β(2R*,3S*),4α,4aβ,10aβ]]-3-(Methanesulfonyl) amino-2-hydroxybenzenepropanoic acid-9-methylene-1,2,3,4,4a,9,10,10a-octahydro-1,12,12-trimethyl-4a,10a-epoxy-1,4-methanophenanthren-2-ylester 7 mg (10 μmol) of the compound that is presented according to Example 26a is reacted analogously to Example 1a. After working-up and purification, 4.8 mg (9.2 μmol, 90%) of the title compound is isolated as a colorless oil.

$^1$H-NMR (CDCl$_3$): δ=0.86 (3H), 0.93 (3H), 1.13 (3H), 1.79 (1H), 2.39 (1H), 2.61 (3H), 2.73 (1H), 2.77 (1H), 2.95 (1H), 3.36 (1H), 4.65 (1H), 4.84 (1H), 4.99 (1H), 5.22 (1H), 5.52 (1H), 6.41 ((1H), 7.20–7.40 (5H), 7.45–7.60 (4H) ppm.

EXAMPLE 26A

[1R-[1α,2β(2R*,3S*),4α,4aβ,10aβ]]-3-(Methanesulfonyl) amino-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 20 mg (33 μmol) of the amine that is presented according to Example 26b is dissolved in 1 ml of anhydrous dichloromethane, mixed at 0° C. under an atmosphere of dry argon with 14 μl of triethylamine, 12 mg of dimethylaminopyridine, 7.7 μl of methanesulfonic acid chloride, and it is stirred for 1 hour. It is mixed with saturated sodium bicarbonate solution, extracted with dichloromethane, the organic phase is washed with saturated sodium chloride solution and dried on magnesium sulfate. The residue that is obtained after filtration and removal of solvent is purified by chromatography on two analytical thin-layer plates. A mixture of n-hexane and ethyl acetate is used as a mobile solvent; a mixture of diethyl ether and 2-propanol is used as an eluant. 7 mg (10.3 μmol, 31%) of the title compound is isolated as a colorless oil.

$^1$H-NMR (CDCl$_3$): δ=0.83 (3H), 0.91 (3H), 1.00–1.22 (24H), 1.61 (1H), 2.28 (1H), 2.68 (4H), 2.72 (1H), 3.31 (1H), 4.81 (1H), 4.83 (1H), 4.97 (1H), 5.18 (1H), 5.51 (1H), 6.51 (1H), 7.2–7.37 (5H), 7.46–7.59 (4H) ppm.

EXAMPLE 26b

[1R-[1α,2β(2R*,3S*),4α,4aβ,10aβ]]-3-Amino-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester The solution of 60 mg (85 μmol) of the compound that is presented according to Example 1a in 0.6 ml of tetrahydrofuran and 0.6 ml of dioxane is mixed at 0° C. with 0.6 ml of a 4N HCl/dioxane solution. It is allowed to heat to 23° C. and after 2 or 3 hours in each case, 0.6 ml of 4N HCl/dioxane solution is added. After another hour, it is poured into 5% sodium hydroxide solution, extracted with diethyl ether, the organic phase is washed with water and dried on magnesium sulfate. The residue that is obtained after filtration and removal of solvent is purified by chromatography on 30 ml of fine silica gel (0.040–0.063 mesh). A mixture of n-hexane and ethyl acetate is used as a mobile solvent, to which 1% triethylamine is added. 21 mg (35 μmol, 41%) of the title compound is isolated as a colorless oil.

$^1$H-NMR (CDCl$_3$): δ=0.82 (3H), 0.85–1.13 (27H), 1.64 (1H), 1.85 (2H), 2.23 (1H), 2.64 (1H), 2.72 (1H), 3.06 (1H), 4.38 (1H), 4.61 (1H), 4.91 (1H), 5.03 (1H), 5.46 (1H), 7.12–7.55 (9H) ppm.

EXAMPLE 27

[1R-[1α,2β(2R*,3S*),4α,4aβ,10aβ]]-3-[[(4-Methylphenyl) sulfonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 8 mg (10.6 μmol) of the compound that is presented according to Example 27a is reacted analogously to Example 1a. After working-up and purification, 4 mg (6.7 μmol, 63%) of the title compound is isolated as a colorless oil.

$^1$H-NMR (CDCl$_3$): δ=0.89 (3H), 0.92 (3H), 1.16 (3H), 1.69 (1H), 2.20 (3H), 2.32 (1H), 2.73 (1H), 2.81 (1H), 2.99 (1H), 3.41 (1H), 4.61 (1H), 4.82 (1H), 4.90 (1H), 5.29 (1H), 5.60 (1H), 6.53 (1H), 6.75 (2H), 6.97–7.11 (3H), 7.15 (2H), 7.30–7.43 (4H), 7.53 (1H), 7.62 (1H) ppm.

EXAMPLE 27a

[1R-[1α,2β(2R*,3S*),4α,4aβ,10aβ]]-3-[[(4-Methylphenyl) sulfonyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester 15 mg (25 μmol) of the compound that is presented according to Example 26b is reacted analogously to Example 26a. After working-up and purification, 6 mg (7.9 μmol, 32%) of the title compound is isolated as a colorless oil.

$^1$H-NMR (CDCl$_3$): δ=0.83 (3H), 0.89 (3H), 0.96–1.17 (24H), 1.40 (1H), 2.16 (1H), 2.24 (3H), 2.63 (1H), 2.76

(1H), 3.35 (1H), 4.71–4.79 (2H), 4.85 (1H), 5.23 (1H), 5.58 (1H), 6.68 (1H), 6.88 (2H), 6.99–7.11 (3H), 7.20–7.40 (5H), 7.48 (3H) ppm.

EXAMPLE 28

[1R-[1α,2β(2R*,3S*),4α,4aβ,10aβ]]-3-[[(Ethylamino) carbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 16 mg (24 μmol) of the compound that is presented according to Example 28a is reacted analogously to Example 1a. After working-up and purification, 7 mg (13.5 μmol, 56%) of the title compound is isolated as a colorless oil.

$^1$H-NMR (CDCl$_3$): δ=0.70 (3H), 1.03 (3H), 1.07 (3H), 1.12 (3H), 2.21 (1H), 2.42 (1H), 2.57 (1H), 2.66 (1H), 2.74 (1H), 2.86 (1H), 3.21 (2H), 4.58 (1H), 4.71 (1H), 5.08 (1H), 5.10 (1H), 5.34 (1H), 5.37 (1H), 6.20 (1H), 7.18–7.50 (9H) ppm.

EXAMPLE 28a

[1R-[1α,2β(2R*,3S*),4α,4aβ,10aβ]]-3-[[(Ethylamino) carbonyl]amino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester The solution of 45 mg (75 μmol) of the amine that is presented according to Example 26b in 2 ml of anhydrous dichloromethane is mixed at 0° C. with 42 μl of triethylamine, 36 mg of dimethylaminopyridine, 23 μl of ethyl isocyanate, and it is stirred for 1 hour. It is purified immediately by chromatography on two analytical thin-layer plates. A mixture of n-hexane and ethyl acetate is used as a mobile solvent; a mixture of diethyl ether and 2-propanol is used as an eluant. 20 mg (30 μmol, 40%) of the title compound is isolated as a colorless oil.

EXAMPLE 29

[1R-[1α,2β(2R*,3S*),4α,4aβ,10aβ]]-3-[[[(1-Methyl) ethylamino]carbonyl]amino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 10 mg (15 μmol) of the compound that is presented according to Example 29a is reacted analogously to Example 1a. After working-up and purification, 4 mg (7.5 μmol, 50%) of the title compound is isolated as a colorless oil.

$^1$H-NMR (CDCl$_3$): δ=0.53 (3H), 0.88 (6H), 0.95 (3H), 1.11 (3H), 1.85 (1H), 2.47 (1H), 2.71 (1H), 2.82 (1H), 2.87 (1H), 3.20 (1H), 3.67 (1H), 4.58 (1H), 4.78 (1H), 5.04 (1H), 5.17 (1H), 5.21 (1H), 5.57 (1H), 6.66 (1H), 7.19–7.42 (7H), 7.58 (2H) ppm.

EXAMPLE 29a

[1R-[1α,2β(2R*,3S*),4α,4aβ,10aβ]]-3-[[[(1-Methyl) ethylamino]carbonyl]amino]-2-(triisopropylsilyloxy) benzenepropanoic acid-9-methylene-1,2,3,4,4a,9,10,10a-octahydro-1,12,12-trimethyl-4a,10a-epoxy-1,4-methanophenanthren-2-ylester 20 mg (33 μmol) of the amine that is presented according to Example 26b is reacted analogously to Example 28a. After working-up and purification, 10 mg (14.5 μmol, 44%) of the title compound is isolated as a colorless oil.

$^1$H-NMR (CDCl$_3$): δ=0.57 (3H), 0.76–1.22 (33H), 1.70 (1H), 2.32 (1H), 2.76 (1H), 2.84 (1H), 3.20 (1H), 3.70 (1H), 4.72 (1H), 4.77 (1H), 4.98 (1H), 5.17 (1H), 5.20 (1H), 5.56 (1H), 6.56 (1H), 7.12–7.42 (7H), 7.56 (2H) ppm.

EXAMPLE 30

[1R-[1α,2β(2R*,3S*),4α,4aβ,10aβ]]-3-(Methoxycarbonyl) amino-2-hydroxybenzenepropanoic acid-9-methylene-1,2, 3,4,4a,9,10,10a-octahydro-1,12,12-trimethyl-4a,10a-epoxy-1,4-methanophenanthren-2-ylester 2.3 mg (3.5 μmol) of compound B that is presented according to Example 23a is reacted analogously to Example 1a. After working-up and purification, 1.6 mg (3.2 μmol, 91%) of the title compound is isolated as a colorless oil.

$^1$H-NMR (CDCl$_3$): δ=0.84 (3H), 0.95 (3H), 1.05 (3H), 1.81 (1H), 2.38 (1H), 2.70 (1H), 2.71 (1H), 3.15 (1H), 3.21 (1H), 3.66 (3H), 4.58 (1H), 5.03 (1H), 5.09 (1H), 5.32 (1H), 5.50 (1H), 5.79 (1H), 7.20–7.56 (9H) ppm.

EXAMPLE 31

[1R-[1α,2β(2R*,3S*),4α,4aβ,10aβ]]-3-(Methylthiocarbonyl)amino-2-hydroxybenzenepropanoic acid-9-methylene-1,2,3,4,4a,9,10,10a-octahydro-1,12,12-trimethyl-4a-ethoxy-10a-hydroxy-1,4-methanophenanthren-2-ylester (A) and
[1S-[1α,2β(2R*,3S*),4α,4aβ,10aβ]]-3-(methylthiocarbonyl)amino-2-hydroxybenzenepropanoic acid-9-methylene-1,2,3,4,4a,9,10,10a-octahydro-1,12,12-trimethyl-4a-ethoxy-10a-hydroxy-1,4-methanophenanthren-2-ylester (B)

The solution of 32 mg (54 μmol) of the mixture that is presented according to Example 31a in 1 ml of ethanol is mixed with 40 μl of a 1N aqueous HCl solution, and it is stirred at 23° C. for 1 hour. It is mixed with saturated sodium bicarbonate solution, extracted with dichloromethane, the organic phase is washed with saturated sodium chloride solution and dried on magnesium sulfate. The residue that is obtained after filtration and removal of solvent is purified by chromatography on two analytical thin-layer plates. A mixture of n-hexane and ethyl acetate is used as a mobile solvent; a mixture of diethyl ether and 2-propanol is used as an eluant. After working-up and purification, 3.2 mg (5.7 μmol, 10%) of title compound as well as 2.5 mg (4.4 μmol, 8%) of title compound B are isolated in each case as a colorless oil.

$^1$H-NMR (CDCl$_3$) of A: δ=0.64 (3H), 0.97 (3H), 1.02 (3H), 1.03 (3H), 2.03 (1H), 2.33 (3H), 2.40 (1H), 2.67 (1H), 2.71 (1H), 2.77 (1H), 2.83 (1H), 3.00 (1H), 3.19 (1H), 4.24 (1H), 4.50 (1H), 5.14 (1H), 5.26 (1H), 5.37 (1H), 5.50 (1H), 7.20–7.50 (9H), 7.72 (1H) ppm.

$^1$H-NMR (CDCl$_3$) of B: δ=0.63 (3H), 0.93–1.12 (9H), 2.14 (1H), 2.35 (3H), 2.39 (1H), 2.70 (2H), 2.77 (1H), 2.86 (1H), 3.01 (1H), 3.08 (1H), 4.18 (1H), 4.53 (1H), 5.13 (1H), 5.21 (1H), 5.36 (1H), 5.55 (1H), 7.20–7.48 (9H), 7.58 (1H) ppm.

EXAMPLE 31a

[1R-[1α,2β(2R*,3S*),4α,4aβ,10aβ]]-3-(Methylthiocarbonyl)amino-2-(3-oxa-pent-2-yloxy) benzenepropanoic acid-9-methylene-1,2,3,4,4a,9,10,10a-octahydro-1,12,12-trimethyl-4a,10a-epoxy-1,4-methanophenanthren-2-ylester (A) and
[1S-[1α,2β(2R*,3S*),4α,4aβ,10aβ]]-3-(methylthiocarbonyl)amino-2-(3-oxa-pent-2-yloxy) benzenepropanoic acid-9-methylene-1,2,3,4,4a,9,10,10a-octahydro-1,12,12-trimethyl-4a,10a-epoxy-1,4-methanophenanthren-2-ylester (B)

30 mg (106 μmol) of the compound that is presented according to Example 1b as well as 49 mg of the β-lactam that is presented according to Example 1q are reacted analogously to Example 1a, and, after working-up and purification, 24 mg (41 μmol, 38%) of the title compounds is obtained as a colorless oil.

EXAMPLE 32

[1R-[1α,2β(2R*,3S*),4α,4aβ,10aβ]]-3-(ethylthiocarbonyl) amino-2-hydroxybenzenepropanoic acid-9-methylene-1,2, 3,4,4a,9,10,10a-octahydro-1,12,12-trimethyl-4a-ethoxy-10a-hydroxy-1,4-methanophenanthren-2-ylester (A) and [1S-[1α,2β(2R*,3S*),4α,4aβ,10aβ]]-3-(ethylthiocarbonyl)amino-2-hydroxybenzenepropanoic acid-9-methylene-1,2,3,4,4a,9,10,10a-octahydro-1,12,12-trimethyl-4a-ethoxy-10a-hydroxy-1,4-methanophenanthren-2-ylester (B)

22 mg (36 μmol) of the mixture that is presented according to Example 32a is reacted analogously to Example 1a. After working-up and purification, 2.5 mg (4.3 μmol, 12%) of title compound A as well as 3 mg (5.2 μmol, 14%) of title compound B are isolated in each case as a colorless oil.

¹H-NMR (CDCl₃) of A: δ=0.63 (3H), 0.95 (3H), 1.00 (3H), 1.02 (3H), 1.27 (3H), 2.03 (1H), 2.39 (1H), 2.66 (1H), 2.70 (1H), 2.76 (1H), 2.78–3.07 (4H), 3.21 (1H), 4.21 (1H), 4.49 (1H), 5.14 (1H), 5.27 (1H), 5.36 (1H), 5.50 (1H), 7.21–7.48 (9H), 7.61 (1H) ppm.

¹H-NMR (CDCl₃) of B: δ=0.64 (3H), 0.96–1.10 (9H), 1.29 (3H), 2.16 (1H), 2.38 (1H), 2.70 (1H), 2.77 (1H), 2.80–3.03 (5H), 3.07 (1H), 4.17 (1H), 4.54-(1H), 5.12 (1H), 5.21 (1H), 5.34 (1H), 5.54 (1H), 7.21–7.55 (10H) ppm.

EXAMPLE 32a

[1R-[1α,2β(2R*,3S*),4α,4aβ,10aβ]]-3-(Ethylthiocarbonyl)amino-2-(3-oxa-pent-2-yloxy)benzenepropanoic acid-9-methylene-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,10aβ]]-3-(ethylthiocarbonyl)amino-2-(3-oxa-pent-2-ylxoy)benzenepropanoic acid-9-methylene-1,2,3,4,4a,9,10,10a-octahydro-1,12,12-trimethyl-4a,10a-epoxy-1,4-methanophenanthren-2-ylester (B)

20 mg (71 μmol) of the compound that is presented according to Example 1b as well as 34 mg of the β-lactam that is presented according to Example 1s are reacted analogously to Example 1a, and, after working-up and purification, 22 mg (36 μmol, 51%) of the title compounds is isolated as a colorless oil.

EXAMPLE 33

[1R-[1α,2β(2R*,3S*),4α,4aβ,9β,10aβ]]-3-(Methoxycarbonyl)amino-2-hydroxybenzenepropanoic acid-9-methyl-1,2,3,4,4a,9,10,10a-octahydro-1,12,12-trimethyl-4a,10a-epoxy-1,4-methanophenanthren-2-ylester (A) and ps [1S-[1α,2β(2R*,3S*),4α,4aβ,9β,10aβ]]-(methoxycarbonyl)amino-2-hydroxybenzenepropanoic acid-9-methyl-1,2,3,4,4a,9,10,10a-octahydro-1,12,12-trimethyl-4a,10a-epoxy-1,4-methanophenanthren-2-ylester (B)

16 mg (24 μmol) of the mixture that is presented according to Example 33a is reacted analogously to Example 1a. After working-up and purification, 3 mg (6 μmol, 25%) of title compound A as well as 3 mg (6 μmol, 25%) of title compound B are isolated in each case as a colorless oil.

¹H-NMR (CDCl₃) of A: δ=0.79 (3H), 0.89 (3H), 1.02 (3H), 1.42 (3H), 1.73 (1H), 2.09 (1H), 2.17 (1H), 2.28 (1H), 2.69 (1H), 3.11 (2H), 3.62 (3H), 4.54 (1H), 4.92 (1H), 5.28 (1H), 6.46 (1H), 7.10–7.59 (9H) ppm.

¹H-NMR (CDCl₃) of B: δ=0.78 (3H), 0.92 (6H), 1.38 (3H), 1.83 (1H), 2.01 (1H), 2.21 (1H), 2.33 (1H), 2.68 (1H), 3.04 (1H), 3.20 (1H), 3.63 (3H), 4.55 (1H), 5.13 (1H), 5.33 (1H), 6.01 (1H), 7.11–7.51 (9H) ppm.

EXAMPLE 33a

[1R-[1α,2β(2R*,3S*),4α,4aβ,9β,10aβ]]-3-(Methoxycarbonyl)amino-2-(triisopropylsilyloxy)benzenepropanoic acid-9-methyl-1,2,3,4,4a,9,10,10a-octahydro-1,12,12-trimethyl-4a,10a-epoxy-1,4-methanophenanthren-2-ylester (A) and [1S-[1α,2β(2R*,3S*),4α,4aβ,9β,10aβ]]-3-(methoxycarbonyl)amino-2-(triisopropylsilyloxy)benzenepropanoic acid-9-methyl-1,2,3,4,4a,9,10,10a-octahydro-1,12,12-trimethyl-4a,10a-epoxy-1,4-methanophenanthren-2-ylester (B)

26 mg (39 μmol) of the mixture that is presented according to Example 23a is reacted analogously to Example 19a. After working-up and purification, 16 mg (24 μmol, 62%) of the title compounds is isolated as a colorless oil.

EXAMPLE 34

[1R-[1α,2β(2R*,3S*),4α,4aβ,9β,10aβ]]-3-(Ethoxycarbonyl)amino-2-hydroxybenzenepropanoic acid-9-methyl-1,2,3,4,4a,9,10,10a-octahydro-1,12,12-trimethyl-4a,10a-epoxy-1,4-methanophenanthren-2-ylester 2 mg (3 μmol) of compound A that is presented according to Example 34a is reacted analogously to Example 1a. After working-up and purification, 1.3 mg (2.5 μmol, 85%) of the title compound is isolated as a colorless oil.

¹H-NMR (CDCl₃): δ=0.78 (3H), 0.90 (3H), 1.07 (3H), 1.21 (3H), 1.43 (3H), 1.60 (1H), 1.75 (1H), 2.30 (1H), 2.47 (1H), 2.74 (1H), 3.00 (1H), 3.15 (1H), 4.10 (2H), 4.52 (1H), 4.83 (1H), 5.28 (1H), 6.89 (1H), 7.13–7.58 (9H) ppm.

EXAMPLE 34a

[1R-[1α,2β(2R*,3S*),4α,4aβ,9β,10aβ]]-3-(Ethoxycarbonyl)amino-2-(triisopropylsilyloxy)benzenepropanoic acid-9-methyl-1,2,3,4,4a,9,10,10a-octahydro-1,12,12-trimethyl-4a,10a-epoxy-1,4-methanophenanthren-2-ylester (A) and [1R-[1α,2β(2R*,3S*),4α,4aβ,9β,10aβ]]-3-(ethoxycarbonyl)amino-2-(triisopropylsilyloxy)benzenepropanoic acid-9-methyl-1,2,3,4,4a,9,10,10a-octahydro-1,12,12-trimethyl-4a,10a-epoxy-1,4-methanophenanthren-2-ylester (B)

102 mg (151 μmol) of the compound that is presented according to Example 24a is reacted analogously to Example 19a. After working-up and purification, 2 mg (3 μmol, 2%) of title compound A as well as 38 mg (56 μmol, 37%) of title compound B are isolated in each case as a colorless oil.

¹H-NMR (CDCl₃) of A: δ=0.72 (3H), 0.75–1.60 (35H), 2.15 (1H), 2.42 (1H), 2.63 (1H), 3.13 (1H), 4.12 (2H), 4.68 (1H), 4.82 (1H), 5.27 (1H), 6.90 (1H), 7.16–7.58 (9H) ppm.

¹H-NMR (CDCl₃) of B: δ=0.75 (3H), 0.80–1.30 (31H), 1.42 (3H), 1.54 (1H), 2.05 (1H), 2.18 (1H), 2.59 (1H), 3.04 (1H), 4.11 (2H), 4.65 (1H), 4.89 (1H), 5.29 (1H), 6.27 (1H), 7.10–7.56 (9H) ppm.

EXAMPLE 35

[1R-[1α,2β(2R*,3S*),4α,4aβ,9β,10aβ]]-3-(Ethoxycarbonyl)amino-2-hydroxybenzenepropanoic acid-9-methyl-1,2,3,4,4a,9,10,10a-octahydro-1,12,12-trimethyl-4a,10a-epoxy-1,4-methanophenanthren-2-ylester 38 mg (56 μmol) of compound B that is presented according to Example 35a is reacted analogously to Example 1a. After working-up and purification, 26 mg (50 μmol, 89%) of the title compound is isolated as a colorless oil.

¹H-NMR (CDCl₃): δ=0.79 (3H), 0.90 (3H), 1.03 (3H), 1.20 (3H), 1.41 (3H), 1.73 (1H), 2.08 (1H), 2.20 (1H), 2.28 (1H), 2.68 (1H), 3.07 (1H), 3.20 (1H), 4.10 (2H), 4.52 (1H), 4.92 (1H), 5.28 (1H), 6.30 (1H), 7.10–7.60 (9H) ppm.

EXAMPLE 36

[1R-1α,2β(2R*,3S*),4α,4aβ,9β,10aβ]-3-(Butoxycarbonyl)amino-2-hydroxybenzenepropanoic acid-9-methyl-1,2,3,4,4a,9,10,10a-octahydro-1,12,12-trimethyl-4a,10a-epoxy-1,4-methanophenanthren-2-ylester 7 mg (10 μmol) of the compound that is presented according to Example 36a is reacted analogously to Example 1a. After working-up and purification, 5 mg (9 μmol, 90%) of the title compound is isolated as a colorless oil.

$^1$H-NMR (CDCl$_3$): δ=0.60–1.62 (19H), 1.74 (1H), 2.07 (1H), 2.19 (1H), 2.30 (1H), 2.68 (1H), 3.07 (1H), 3.19 (1H), 3.80 (1H), 4.03 (1H), 4.53 (1H), 4.93 (1H), 5.27 (1H), 6.25 (1H), 7.10–7.58 (9H) ppm.

EXAMPLE 36a
[1R-[1α,2β(2R*,3S*),4α,4aβ,9β,10aβ]]-3-(Butoxycarbonyl)amino-2-(triisopropylsilyloxy) benzenepropanoic acid-9-methyl-1,2,3,4,4a,9,10,10a-octahydro-1,12,12-trimethyl-4a,10a-epoxy-1,4-methanophenanthren-2-ylester 20 mg (28 μmol) of the compound that is presented according to Example 25a is reacted analogously to Example 19a. After working-up and purification, 7 mg (10 μmol, 36%) of the title compound is isolated as a colorless oil.

$^1$H-NMR (CDCl$_3$): δ=0.68–1.61 (42H), 2.03 (1H), 2.16 (1H), 2.59 (1H), 3.05 (1H), 3.83 (1H), 4.05 (1H), 4.66 (1H), 4.87 (1H), 5.27 (1H), 6.23 (1H), 7.07–7.50 (9H) ppm.

EXAMPLE 37
[1R-[1α,2β(2R*,3S*),4α,4aβ,9β,10aβ]]-3-[(1-Oxobutyl) amino]-2-hydroxybenzenepropanoic acid-9-methyl-1,2,3,4,4a,9,10,10a-octahydro-1,12,12-trimethyl-4a,10a-epoxy-1,4-methanophenanthren-2-ylester 24 mg (36 μmol) of the compound that is presented according to Example 37a is reacted analogously to Example 1a. After working-up and purification, 13 mg (25 μmol, 70%) of the title compound is isolated as a colorless oil.

$^1$H-NMR (CDCl$_3$): δ=0.78 (3H), 0.82 (3H), 0.90 (3H), 0.98 (3H), 1.35 (3H), 1.62 (2H), 1.81 (1H), 2.10 (2H), 2.23 (2H), 2.32 (1H), 2.69 (1H), 3.08 (1H), 3.30 (1H), 4.54 (1H), 5.07 (1H), 5.49 (1H), 7.03 (1H), 7.12–7.33 (6H), 7.39 (2H), 7.48 (1H) ppm.

EXAMPLE 37a
[1R-[1α,2β(2R*,3S*),4α,4aβ,9β,10aβ]]-3-[(1-Oxobutyl) amino]-2-(triisopropylsilyloxy)benzenepropanoic acid-9-methyl-1,2,3,4,4a,9,10,10a-octahydro-1,12,12-trimethyl-4a,10a-epoxy-1,4-methanophenanthren-2-ylester 60 mg (89 μmol) of the compound that is presented according to Example 13a is reacted analogously to Example 19a. After working-up and purification, 24 mg (36 μmol, 40%) of the title compound is isolated as a colorless oil.

$^1$H-NMR (CDCl$_3$): δ=0.75 (3H), 0.78–1.18 (30H), 1.38 (3H), 1.57–1.74 (3H), 2.08 (2H), 2.22 (1H), 2.28 (3H), 2.62 (1H), 3.05 (1H), 4.63 (1H), 4.96 (1H), 5.51 (1H), 6.98 (1H), 7.09–7.40 (8H), 7.46 (1H) ppm.

EXAMPLE 38
[1R-[1α,2β(2R*,3S*),4α,4aβ,9β,10aβ]]-3-[3-Cyclopentyl-1-oxopropyl)amino]-2-hydroxybenzenepropanoic acid-9-methyl-1,2,3,4,4a,9,10,10a-octahydro-1,12,12-trimethyl-4a,10a-epoxy-1,4-methanophenanthren-2-ylester (A) and
[1S-[1α,2β(2R*,3S*),4α,4aβ,9β,10aβ]]-3-[3-cyclopenytl-1-oxopropyl)amino]-2-hydroxybenzenepropanoic acid-9-methyl-1,2,3,4,4a,9,10,10a-octahydro-1,12,12-trimethyl-4a,10a-epoxy-1,4-methanophenanthren-2-ylester (B)

10 mg (14 μmol) of the mixture that is presented according to Example 38a is reacted analogously to Example 1a. After working-up and purification, 2 mg (3.5 μmol, 25%) of title compound A as well as 2.4 mg (4.2 μmol, 30%) of title compound B are isolated in each case as a colorless oil.

$^1$H-NMR (CDCl$_3$) of A: δ=0.79 (3H), 0.83–1.04 (8H), 1.30–1.70 (12H), 1.83 (1H), 2.09 (2H), 2.27 (2H), 2.35 (1H), 2.70 (1H), 3.08 (1H), 3.29 (1H), 4.56 (1H), 5.09 (1H), 5.45 (1H), 7.10–7.43 (9H), 7.48 (1H) ppm.

$^1$H-NMR (CDCl$_3$) of B: δ=0.77 (3H), 0.84–1.07 (8H), 1.32 (3H), 1.38–1.70 (9H), 1.81 (1H), 1.98 (1H), 2.08 (1H), 2.24 (2H), 2.33 (1H), 2.68 (1H), 3.03 (1H), 3.16 (1H), 4.53 (1H), 5.17 (1H), 5.66 (1H), 6.96 (1H), 7.10–7.48 (9H) ppm.

EXAMPLE 38a
[1R-[1α,2β(2R*,3S*),4α,4aβ,9β,10aβ]]-3-[3-Cyclopentyl-1-oxopropyl)amino]-2-(triisopropylsilyloxy) benzenepropanoic acid-9-methyl-1,2,3,4,4a,9,10,10a-octahydro-1,12,12-trimethyl-4a,10a-epoxy-1,4-methanophenanthren-2-ylester (A) and
[1S-[1α,2β(2R*,3S*),4α,4aβ,9β,10aβ]]-3-[3-Cyclopentyl-1-oxopropyl)amino]-2-(triisopropylsilyloxy) benzenepropanoic acid-9-methyl-1,2,3,4,4a,9,10,10a-octahydro-1,12,12-trimethyl-4a,10a-epoxy-1,4-methanophenanthren-2-ylester (B)

18 mg (25 μmol) of the mixture that is presented according to Example 20a is reacted analogously to Example 19a. After working-up and purification, 10 mg (14 μmol, 56%) of the title compounds is isolated as a colorless oil.

EXAMPLE 39
[1R-[1α,2β(2R*,3S*),4α,4aβ,9β,10aβ]]-3-[[[(1-Methyl) ethylamino]carbonyl]amino]-2-hydroxybenzenepropanoic acid-9-methyl-1,2,3,4,4a,9,10,10a-octahydro-1,12,12-trimethyl-4a,10a-epoxy-1,4-methanophenanthren-2-ylester 4 mg (6 μmol) of the compound that is presented according to Example 39a is reacted analogously to Example 1a. After working-up and purification, 2 mg (3.8 μmol, 63%) of the title compound is isolated as a colorless oil.

$^1$H-NMR (CDCl$_3$): δ=0.65 (3H), 0.71 (3H), 0.84 (3H), 0.95 (3H), 1.07 (3H), 1.40 (3H), 1.83 (1H), 2.19 (2H), 2.46 (1H), 2.75 (1H), 2.93 (1H), 3.13 (1H), 3.67 (1H), 4.58 (1H), 4.77 (1H), 5.08 (1H), 5.13 (1H), 6.20 (1H), 7.14–7.36 (8H), 7.49 (1H) ppm.

EXAMPLE 39a
[1R-[1α,2β(2R*,3S*),4α,4aβ,9β,10aβ]]-3-[[[(1-Methyl) ethylamino]carbonyl]amino]-2-(triisopropylsilyloxy) benzenepropanoic acid-9-methyl-1,2,3,4,4a,9,10,10a-octahydro-1,12,12-trimethyl-4a,10a-epoxy-1,4-methanophenanthren-2-ylester 10 mg (15 μmol) of the compound that is presented according to Example 29a is reacted analogously to Example 19a. After working-up and purification, 4 mg (6 μmol, 40%) of the title compound is isolated as a colorless oil.

$^1$H-NMR (CDCl$_3$): δ=0.65 (6H), 0.75–1.15 (30H), 1.39 (3H), 1.72 (1H), 2.18 (2H), 2.38 (1H), 2.70 (1H), 3.11 (1H), 3.68 (1H), 4.68 (2H), 4.97 (1H), 5.20 (1H), 6.04 (1H), 7.12–7.36 (8H), 7.47 (1H) ppm.

EXAMPLE 40
[1R-[1α,2β(2R*,3S*),4α,4aβ,9β,10aβ]]-3-[(1-Oxobutyl) methylamino]-2-hydroxybenzenepropanoic acid-9-methylene-1,2,3,4,4a,9,10,10a-octahydro-1,12,12-trimethyl-4a,10a-epoxy-1,4-methanophenanthren-2-ylester 9 mg (13 μmol) of the compound that is presented according to Example 40a is reacted analogously to Example 1a. After working-up and purification, 5.6 mg (10.6 μmol, 81%) of the title compound is isolated as a colorless oil.

$^1$H-NMR (CDCl$_3$): δ=0.80 (3H), 0.87–1.06 (9H), 1.53–1.83 (3H), 2.22–2.40 (3H), 2.65 (1H), 2.70 (1H), 2.91 (3H), 3.02 (1H), 4.83 (2H), 5.02 (1H), 5.05 (1H), 5.46 (1H), 5.72 (1H), 7.21–7.40 (7H), 7.45 (1H), 7.50 (1H) ppm.

EXAMPLE 40a

[1R-[1α,2β(2R*,3S*),4α,4aβ,9β,10aβ]]-3-[(1-Oxobutyl) methylamino]-2-(triisopropylsilyloxy)benzenepropanoic acid-9-methylene-1,2,3,4,4a,9,10,10a-octahydro-1,12,12-trimethyl-4a,10a-epoxy-1,4-methanophenanthren-2-ylester The solution of 15 mg (22 μmol) of the compound that is presented according to Example 13a in 0.3 ml of anhydrous tetrahydrofuran is added to 1 mg of a 60% oily sodium hydride dispersion under an atmosphere of dry argon, mixed with 2.1 μl of iodomethane and stirred for 2 hours at 23° C. After working-up, 9 mg (13 μmol, 60%) of the title compound is isolated as a colorless oil, which is immediately further reacted.

EXAMPLE 41

[1R-[1α,2β(2R*,3S*),4α,4aβ,9β,10aβ]]-3-[(1-Oxobutyl) amino]-2-acetoxybenzenepropanoic acid-9-methylene-1,2,3,4,4a,9,10,10a-octahydro-1,12,12-trimethyl-4a,10a-epoxy-1,4-methanophenanthren-2-ylester The solution of 11 mg (21 μmol) of the compound, presented according to Example 13, in 0.5 ml of anhydrous pyridine is mixed with 19 μl of acetic anhydride, and it is stirred at 23° C. for 1 hour under an atmosphere of dry argon. It is poured into a saturated sodium bicarbonate solution, extracted with dichloromethane, the organic phase is washed with saturated sodium chloride solution and dried on magnesium sulfate. The residue that is obtained after filtration and removal of solvent is purified by chromatography on an analytical thin-layer plate. A mixture of n-hexane and ethyl acetate is used as a mobile solvent; a mixture of diethyl ether and 2-propanol is used as an eluant. 8 mg (14 μmol, 68%) of the title compound is isolated as a colorless oil.

$^1$H-NMR (CDCl$_3$): δ=0.80 (3H), 0.83 (3H), 0.89 (3H), 1.07 (3H), 1.48 (1H), 1.60 (2H), 2.10–2.30 (3H), 2.20 (3H), 2.68 (1H), 2.81 (1H), 3.07 (1H), 4.97 (1H), 5.02 (1H), 5.32 (1H), 5.52 (1H), 5.69 (1H), 7.20–7.64 (10H) ppm.

We claim:

1. A borneol derivatives of general formula I

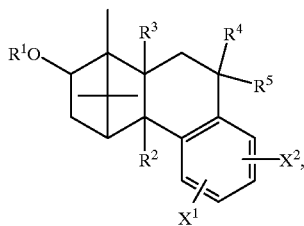

in which

R$^1$ means C(O)—CH(OR$^6$)—CH(NHR$^{7a}$R$^{7b}$)—R$^8$, C(O)—CH(OR$^{6a}$)—CH[NH(C(O)—CH(OR$^{6b}$)—CH(NR$^{7a}$R$^{7b}$)R$^8$)]—R$^8$, R$^2$ means hydrogen, —OH, C$_1$–C$_{10}$ alkyl, C$_1$–C$_{10}$ alkoxy, —OC(O)R$^{9a}$, —OSO$_2$R$^{9a}$, —OP(O)(OH)$_2$, NHR$^{9a}$, NR$^{9a}$R$^{9b}$, R$^3$ means hydrogen, —OH, C$_1$–C$_{10}$ alkoxy, —OC(O)R$^{9b}$, —OSO$_2$R$^{9b}$, —OP(O)(OH)$_2$, or R$^2$, R$^3$ together mean an oxygen atom, R$^4$ means hydrogen, C$_1$–C$_{10}$ alkyl, —(CH$_2$)$_n$—OR$^{11a}$, R$^5$ means hydrogen, C$_1$–C$_{10}$ alkyl, —(CH$_2$)$_p$—OR$^{11b}$, or R$^4$, R$^5$ together mean an oxygen atom, a =CHR$^{10}$ group, R$^{6a}$, R$^{6b}$ are the same or different and mean R$^6$, R$^{7a}$, R$^{7b}$ are the same or different and mean R$^7$, n means 0 to 8, p means 1 to 8, R$^7$ means —C(O)R$^{12}$, —SO$_2$R$^{12}$, —C(O)OR$^{12}$, —C(O)SR$^{12}$, —C(O)NHR$^{9d}$, —C(O)NR$^{9d}$R$^{9e}$, C$_1$–C$_{10}$ alkyl,

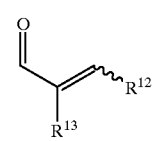

R$^8$ means phenyl,

R$^{9a-e}$, R$^{12}$ are the same or different and mean C$_1$–C$_{10}$ alkyl, C$_4$–C$_8$ cycloalkyl, aryl, C$_7$–C$_{16}$ aralkyl, R$^{10}$ means hydrogen, C$_1$–C$_{10}$ alkyl, —(CH$_2$)$_s$—OR$^{14}$, s means 1 to 8, R$^6$, R$^{11a,b}$, R$^{14}$ are the same or different and mean hydrogen, C$_1$–C$_{10}$ alkyl, aryl, C$_1$–C$_{10}$ acyl, C$_7$–C$_{16}$ aralkyl, —SO$_2$R$^{9c}$, —P(O)(OH)$_2$, R$^{13}$, R$^{15a,b}$ are the same or different and mean hydrogen, C$_1$–C$_{10}$ alkyl, aryl, C$_7$–C$_{16}$ aralkyl, X$^1$, X$^2$ are the same or different and mean X, X means hydrogen, halogen, —OH, —NO$_2$, —N$_3$, —CN, —NR$^{15a}$R$^{15b}$, —NHSO$_2$R$^{15a}$, —CO$_2$R$^{15}$, C$_1$–C$_{10}$ alkyl, C$_1$–C$_{10}$ alkoxy, C$_1$–C$_{10}$ acyloxy, C$_1$–C$_{10}$ acyl, and, if R$^{15}$ means hydrogen, their salts with physiologically compatible bases, as well as the α-, β- or γ-cyclodextrin clathrates, as well as the compounds of general formula I that are encapsulated with liposomes.

2. Pharmaceutical agents that consist of one or more compounds of claim 1 and adjuvants, vehicles and additives that are commonly used.

3. A process for the production of a borneol compound of formula I according to claim 1, which comprises epoxidating an olefin of formula II

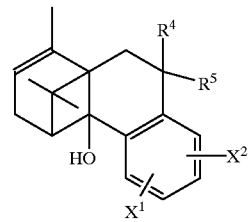

in which R$^4$, R$^5$, X$^1$ and X$^2$ have the above-mentioned meanings and hydroxyl groups that are contained in X$^1$ or X$^2$ are optionally protected, then rearranging the epoxide formed without isolation into an alcohol, of formula III

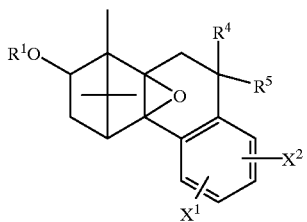

III in which $R^4$, $R^5$, $X^1$ and $X^2$ have the above-mentioned meanings and hydroxyl groups that are contained in $R^1$, $X^1$ or $X^2$ are optionally protected, and converting this rearranged product into a compound of formula I.

4. A compound according to claim 1, wherein:
   each aryl is selected from the group consisting phenyl, naphthyl, furyl, thienyl, pyridyl, pyrazolyl, pyrimidinyl, oxazolyl, pyridazinyl, pyrazinyl and quinolyl, each optionally substituted by halogen, —OH, —NO$_2$, —N$_3$, —CN, —NR$^{15a}$R$^{15b}$, —NHSO$_2$R$^{15a}$, —CO$_2$R$^{15}$, C$_1$-C$_{10}$ alkyl, C$_1$-C$_{10}$ alkoxy, C$_1$-C$_{10}$ acyloxy or C$_1$-C$_{10}$ acyl; and
   each aralkyl group is selected from the group consisting of benzyl, phenylethyl, naphthylmethyl and naphthylethyl, each optionally substituted by halogen, —OH, —NO$_2$, —N$_3$, —CN, —NR$^{15a}$R$^{15b}$, —NHSO$^{15a}$, —CO$_2$R$^{15}$, C$_1$-C$_{10}$ alkyl, C$_1$-C$_{10}$ alkoxy, C$_1$-C$_{10}$ acyloxy or C$_1$-C$_{10}$ acyl.

5. A compound according to claim 1, wherein each acyl group is selected from the group consisting of acetyl, propionyl, butyryl or benzoyl.

6. A compound according to claim 4, wherein each acyl group is selected from the group consisting of acetyl, propionyl, butyryl or benzoyl.

7. The process of claim 3, wherein the epoxidating of the olefin of formula II is carried out with a peroxy compound, optionally in the presence of a Lewis acid, in an inert solvent at −40° C. to +40° C.

8. The process of claim 7, wherein the peroxy compound is meta-chloroperbenzoic acid, peroxotrifluoroacetic acid, hydrogen peroxide, tert-butyl hydroperoxide; the Lewis acid, if used, is titanium triisopropoxide; and the inert solvent is dichloromethane or toluene.

9. The process of claim 3, wherein the rearranging of the epoxide formed is catalyzed by an acid.

10. The process of claim 9, wherein the acid is para-toluenesulfonic acid, silica gel, an acid ion exchange resin or hydrochloric acid.

11. The process of claim 3, wherein the converting of the rearranged product into the compound of formula I is by:
    esterification of the alcohol function, where $R^1$=hydrogen, followed by modification of $R^4$ and/or $R^5$, optionally followed by epoxide opening, if $R^2$ and $R^3$ together represent an oxygen atom, and optionally with subsequent modification of $R^2$ and $R^3$.

12. The process of claim 3, wherein the converting of the rearranged product into the compound of formula I is by:
    esterification of alcohol function, where $R^1$=hydrogen, optionally followed by epoxide opening, if $R^2$ and $R^3$ together represent an oxygen atom, optionally with subsequent modification of $R^2$ and $R^3$, and modification of $R^4$ and/or $R^5$.

13. The process of claim 3, wherein the converting of the rearranged product into the compound of formula I is by:
    protection of alcohol function, where $R^1$=hydrogen, optionally followed by epoxide opening, if $R^2$ and $R^3$ together represent an oxygen atom, optionally with subsequent modification of $R^2$ and $R^3$, followed by modification of $R^4$ and/or $R^5$, and release and subsequent esterification of alcohol function, where $R^1$=hydrogen.

14. The process of claim 3, wherein the converting of the rearranged product into the compound of formula I is by:
    protection of alcohol function, where $R^1$=hydrogen, followed by modification of $R^4$ and/or $R^5$, followed by release and subsequent esterification of the alcohol function, where $R^1$=hydrogen, optionally followed by epoxide opening, if $R^2$ $R^3$ together represent an oxygen atom, and optionally with subsequent modification of $R^2$ and $R^3$.

15. A pharmaceutical agent according to claim 2, wherein the compound of formula I is present in an amount of 0.1–100 mg per dosage unit.

* * * * *